US010751704B2

(12) United States Patent
Tomishige et al.

(10) Patent No.: US 10,751,704 B2
(45) Date of Patent: Aug. 25, 2020

(54) HYDROGENATION REACTION CATALYST FOR 1,4-ANHYDROERYTHRITOL, METHOD FOR PRODUCING 3-HYDROXYTETRAHYDROFURAN, AND METHOD FOR PRODUCING 1,3-BUTANE DIOL

(71) Applicant: DAICEL CORPORATION, Osaka-shi, Osaka (JP)

(72) Inventors: Keiichi Tomishige, Sendai (JP);
Yoshinao Nakagawa, Sendai (JP);
Yasuteru Kajikawa, Himeji (JP);
Yuuichirou Hirai, Himeji (JP)

(73) Assignee: DAICEL CORPORATION, Osaka-Shi (JP)

( * ) Notice: Subject to any disclaimer, the term of this patent is extended or adjusted under 35 U.S.C. 154(b) by 0 days.

(21) Appl. No.: 16/409,279

(22) Filed: May 10, 2019

(65) Prior Publication Data
US 2019/0262805 A1 Aug. 29, 2019

Related U.S. Application Data

(62) Division of application No. 14/436,357, filed as application No. PCT/JP2013/079406 on Oct. 30, 2013, now abandoned.

(30) Foreign Application Priority Data

Nov. 13, 2012 (JP) ................................. 2012-249653

(51) Int. Cl.
| | | |
|---|---|---|
| B01J 23/888 | (2006.01) | |
| B01J 23/30 | (2006.01) | |
| C07C 29/132 | (2006.01) | |
| C07D 307/20 | (2006.01) | |
| B01J 35/00 | (2006.01) | |
| B01J 23/652 | (2006.01) | |
| B01J 23/656 | (2006.01) | |
| B01J 29/48 | (2006.01) | |
| B01J 23/44 | (2006.01) | |
| B01J 21/18 | (2006.01) | |
| B01J 37/02 | (2006.01) | |
| B01J 37/04 | (2006.01) | |

(52) U.S. Cl.
CPC ............ *B01J 23/888* (2013.01); *B01J 23/30* (2013.01); *B01J 23/44* (2013.01); *B01J 23/6527* (2013.01); *B01J 23/6567* (2013.01); *B01J 29/48* (2013.01); *B01J 35/0006* (2013.01); *C07C 29/132* (2013.01); *C07D 307/20* (2013.01); *B01J 21/18* (2013.01); *B01J 37/0201* (2013.01); *B01J 37/04* (2013.01); *Y02P 20/588* (2015.11)

(58) Field of Classification Search
CPC ...... C07C 29/132; C07C 31/207; B01J 21/18; B01J 23/30; B01J 23/44; B01J 23/6527; B01J 23/6567; B01J 23/888; B01J 29/48; B01J 35/0006; B01J 37/0201; B01J 37/04; C07D 307/20
See application file for complete search history.

(56) References Cited

U.S. PATENT DOCUMENTS

| | | |
|---|---|---|
| 4,585,748 A | 4/1986 | Usui et al. |
| 6,593,481 B1 | 7/2003 | Manzer |
| 2011/0151354 A1 | 6/2011 | Jin et al. |

FOREIGN PATENT DOCUMENTS

WO WO 03/042201 A1 5/2003

OTHER PUBLICATIONS

Chen et al., "C—O bond hydrogenolysis of cyclic ethers with OH groups over rhenium-modified supported iridium catalysts", Journal of Catalysis, vol. 294, (2012), pp. 171-183.
International Search Report, issued in PCT/JP2013/079406, dated Jan. 28, 2014.
Nakagawa et al., "Direct hydrogenolysis of glycerol into 1,3-propanediol over rhenium-modified iridium catalyst", Journal of Catalysis, vol. 272, (2010), pp. 191-194.
Eibl et al., Langmuir, vol. 17, pp. 107-115, 2001.
Feng et al., Journal of Power Sources, vol. 196, pp. 2464-2474, 2011.
Taylor et al., Journal of Catalysis, vol. 285, pp. 103-114, Oct. 20, 2011.
Whitelocke et al., AIChE Annual Meeting, Conference Proceedings, Philadelphia, PA, Nov. 16-21, 2008.
Ye et al., Journal of Power Sources, vol. 195, pp. 2633-2637, 2010.
Zhang et al., Electrochemistry Comm., vol. 10, pp. 1113-1116, 2008.
Zhang et al., Journal of Catalysis, vol. 138, pp. 55-69, 1992.

*Primary Examiner* — Valerie Rodriguez-Garcia
(74) *Attorney, Agent, or Firm* — Birch, Stewart, Kolasch & Birch, LLP

(57) ABSTRACT

A hydrogenation reaction catalyst used for a reaction of 1,4-anhydroerythritol and hydrogen to produce 3-hydroxytetrahydrofuran includes a carrier, at least one oxide selected from the group consisting of an oxide of a Group 6 element and an oxide of a Group 7 element, the oxide being supported on the carrier, and a metal other than a Group 6 element and a Group 7 element, the other metal being supported on the carrier. The amount of the oxide supported on the carrier in terms of a metal atom forming the oxide is 0.01 to 10% by weight based on the total amount of the oxide and the carrier being 100% by weight. The molar ratio in terms of metal of the other metal to the Group 6 element and Group 7 element forming the oxide [other metal/Group 6 element and Group 7 element] is 50/1 to 1/4.

16 Claims, 1 Drawing Sheet

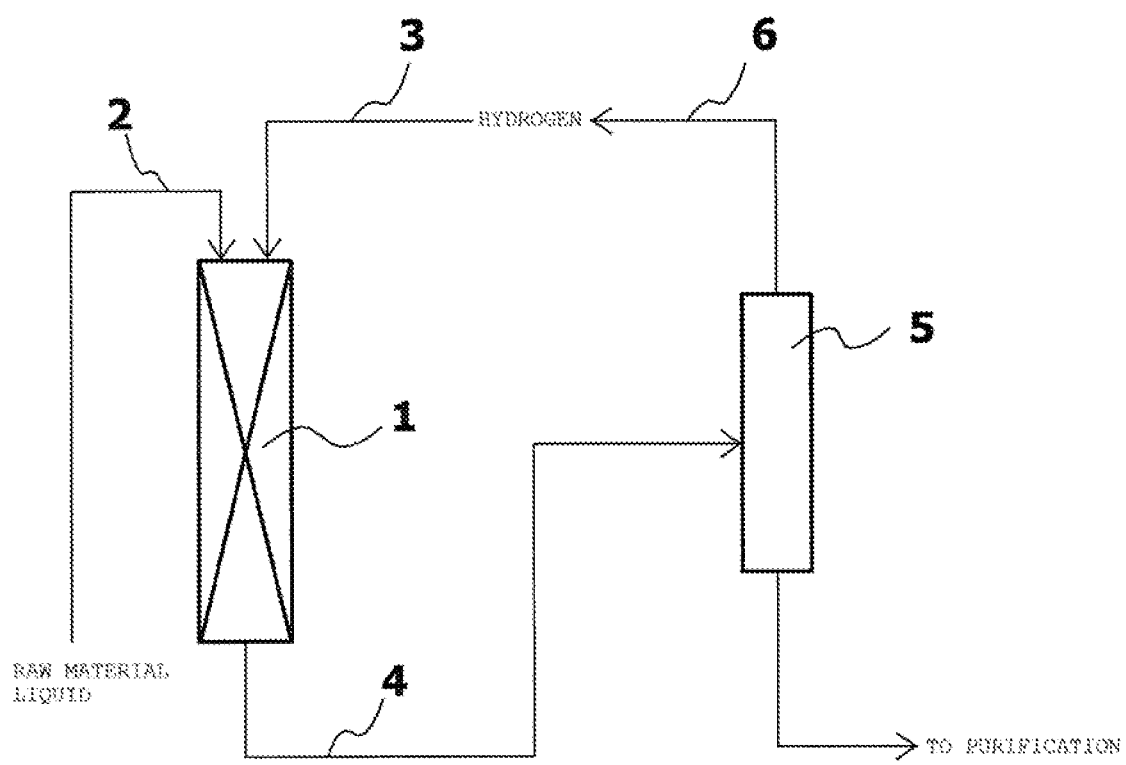

HYDROGENATION REACTION CATALYST FOR 1,4-ANHYDROERYTHRITOL, METHOD FOR PRODUCING 3-HYDROXYTETRAHYDROFURAN, AND METHOD FOR PRODUCING 1,3-BUTANE DIOL

CROSS REFERENCE TO RELATED APPLICATIONS

This application is a Divisional of copending application Ser. No. 14/436,357, filed on Apr. 16, 2015, which is a national phase of PCT International Application No. PCT/JP2013/079406, filed on Oct. 30, 2013, which claims the benefit under 35 U.S.C. § 119(a) to Patent Application No. 2012-249653, filed in Japan on Nov. 13, 2012, all of which are hereby expressly incorporated by reference into the present application.

TECHNICAL FIELD

The present invention relates to a method for producing 3-hydroxytetrahydrofuran using 1,4-anhydroerythritol as a raw material. The present invention also relates to a method for producing 1,3-propane diol using 3-hydroxytetrahydrofuran as a raw material. The present application claims the priority to Japanese Patent Application No. 2012-249653 filed on Nov. 13, 2012 in Japan, the content of which is herein incorporated.

BACKGROUND ART

Currently, in order to produce chemicals, chemical fuel resources such as petroleum are mainly consumed in large amounts. That is, carbon is currently released from the earth to the atmosphere unilaterally in today's society. Therefore, the problems of global warming, depletion of fossil fuel resources, and the like have been caused, and in response to such problems, there has been recently demanded for building of a sustainable society by utilizing so-called biomass (plant-based resources such as cellulose, glucose and vegetable oil) in which carbon is reused and recycled with the help of plant photosynthesis.

In order to realize such a sustainable society described above, it is important to establish a technique for producing useful chemicals from biomass. As such a technique which has been already put in practical use, for example, a technique for producing ethanol by microbial fermentation is known which involves using glucose as a raw material. Ethanol thus obtained is called bioethanol, and is widely utilized as fuel for automobiles and the like. In addition, chemicals produced from a C2 fraction obtained hitherto by naphtha cracking have been recently started to be replaced with chemicals produced from biomass, and for example, it has been possible to produce polyethylene from ethylene obtained by dehydration of bioethanol, and also to produce propylene from ethylene produced from bioethanol.

As other examples, a technique for producing biodiesel fuel from vegetable oil such as palm oil is also put in practical use. Furthermore, a possibility is also studied that glycerol as a by-product in production of the biodiesel fuel is used as a basic chemical raw material for producing a compound including 3 carbon atoms (C3 compound; for example, propylene, 1,2-propane diol, or 1,3-propane diol) (see, for example, Non Patent Literature 1).

CITATION LIST

Non Patent Literature

Non Patent Literature 1: Yoshinao Nakagawa, et al., "Direct hydrogenolysis of glycerol into 1,3-propanediol over rhenium-modified iridium catalyst", Journal of Catalysis, 2010, 272, p. 191-194.

SUMMARY OF INVENTION

Technical Problem

On the other hand, a technique for producing a compound including 4 carbon atoms (C4 compound) from biomass is also studied, but is not still in practical use. In particular, 1,3-butane diol among the C4 compounds is incorporated as a moisturizer or the like into cosmetics, detergents, shampoos, and the like, and is also expected to be used as a raw material for medicines, food additives, various solvents, and the like. Therefore, there is strongly demanded for developing a technique for producing 1,3-butane diol using biomass as a starting material.

The present inventors have focused on 3-hydroxytetrahydrofuran, which is also a compound having 4 carbon atoms, as a raw material of 1,3-butane diol, and have found that the 3-hydroxytetrahydrofuran can be reacted with hydrogen to thereby produce 1,3-butane diol. A technique for producing 3-hydroxytetrahydrofuran using biomass as a starting material, however, is not still known currently.

Accordingly, an object of the present invention is to provide a method for producing 3-hydroxytetrahydrofuran that can be used as a raw material for 1,3-butane diol, using as a raw material a compound that can be derived from biomass.

Another object of the present invention is to provide a method for producing 1,3-butane diol using 3-hydroxytetrahydrofuran as a raw material.

Solution to Problem

The present inventors have made intensive studies in order to solve the above problems, and as a result, have found that 1,4-anhydroerythritol, which can be more easily derived from erythritol of biomass, can be used as a raw material and reacted with hydrogen to thereby produce 3-hydroxytetrahydrofuran at a high selectivity. The present inventors have also found that 3-hydroxytetrahydrofuran can be used as a raw material and reacted with hydrogen to thereby produce 1,3-butane diol at a high selectivity. The present invention has been completed based on such findings.

That is, the present invention provides a method for producing 3-hydroxytetrahydrofuran, including a step of reacting 1,4-anhydroerythritol and hydrogen to produce 3-hydroxytetrahydrofuran.

The present invention further provides the method for producing 3-hydroxytetrahydrofuran, in which the step of reacting 1,4-anhydroerythritol and hydrogen is allowed to proceed in the presence of a catalyst including a carrier and at least one oxide selected from the group consisting of an oxide of a Group 6 element and an oxide of a Group 7 element, the oxide being supported on the carrier.

The present invention further provides the method for producing 3-hydroxytetrahydrofuran, in which the carrier is activated carbon or an inorganic oxide.

The present invention further provides the method for producing 3-hydroxytetrahydrofuran, in which the catalyst further includes a metal other than a Group 6 element and a Group 7 element, the metal being supported on the carrier.

The present invention further provides the method for producing 3-hydroxytetrahydrofuran, in which the metal is at least one metal selected from the group consisting of palladium, platinum, iron, cobalt, nickel and copper.

The present invention further provides the method for producing 3-hydroxytetrahydrofuran, in which the inorganic oxide is at least one inorganic oxide selected from the group consisting of titania, zirconia, magnesia, silica and alumina.

The present invention also provides a hydrogenation reaction catalyst for 1,4-anhydroerythritol, in which the hydrogenation reaction catalyst is use for a reaction of 1,4-anhydroerythritol and hydrogen to produce 3-hydroxytetrahydrofuran, and includes a carrier and at least one oxide selected from the group consisting of an oxide of a Group 6 element and an oxide of a Group 7 element, the oxide being supported on the carrier.

The present invention further provides the hydrogenation reaction catalyst, in which the carrier is activated carbon or an inorganic oxide.

The present invention further provides the hydrogenation reaction catalyst further including a metal other than a Group 6 element and a Group 7 element, the metal being supported on the carrier.

The present invention further provides the hydrogenation reaction catalyst, in which the metal is at least one metal selected from the group consisting of palladium, platinum, iron, cobalt, nickel and copper.

The present invention further provides the hydrogenation reaction catalyst, in which the inorganic oxide is at least one inorganic oxide selected from the group consisting of titania, zirconia, magnesia, silica and alumina.

The present invention also provides a method for producing 1,3-butane diol, including a step of reacting 3-hydroxytetrahydrofuran and hydrogen to produce 1,3-butane diol.

The present invention further provides the method for producing 1,3-butane diol, in which the step of reacting 3-hydroxytetrahydrofuran and hydrogen is allowed to proceed in the presence of a catalyst including a carrier and at least one metal selected from the group consisting of iridium, rhenium, ruthenium, molybdenum and tungsten, the metal being supported on the carrier.

The present invention further provides the method for producing 1,3-butane diol, in which the carrier is an inorganic oxide.

The present invention further provides the method for producing 1,3-butane diol, in which the inorganic oxide is at least one inorganic oxide selected from the group consisting of silica, magnesia, titania and alumina.

The present invention further provides the method for producing 1,3-butane diol, in which the 3-hydroxytetrahydrofuran is 3-hydroxytetrahydrofuran produced by a reaction of 1,4-anhydroerythritol and hydrogen.

The present invention further provides the method for producing 1,3-butane diol, further including, before the step, a step of reacting 1,4-anhydroerythritol and hydrogen to produce 3-hydroxytetrahydrofuran.

The present invention also provides a hydrogenation reaction catalyst for 3-hydroxytetrahydrofuran, in which the hydrogenation reaction catalyst is used for a reaction of 3-hydroxytetrahydrofuran and hydrogen to produce 1,3-butane diol, and includes a carrier and at least one metal selected from the group consisting of iridium, rhenium, ruthenium, molybdenum and tungsten, the metal being supported on the carrier.

The present invention further provides the hydrogenation reaction catalyst, in which the carrier is an inorganic oxide.

The present invention further provides the hydrogenation reaction catalyst, in which the inorganic oxide is at least one inorganic oxide selected from the group consisting of silica, magnesia, titania and alumina.

That is, the present invention relates to the following.

(1) A method for producing 3-hydroxytetrahydrofuran, including a step of reacting 1,4-anhydroerythritol and hydrogen to produce 3-hydroxytetrahydrofuran.

(2) The method for producing 3-hydroxytetrahydrofuran according to (1), in which the step of reacting 1,4-anhydroerythritol and hydrogen is allowed to proceed in the presence of a catalyst including a carrier and at least one oxide selected from the group consisting of an oxide of a Group 6 element and an oxide of a Group 7 element, the oxide being supported on the carrier.

(3) The method for producing 3-hydroxytetrahydrofuran according to (2), in which the oxide is tungsten oxide.

(4) The method for producing 3-hydroxytetrahydrofuran according to (2) or (3), in which the carrier is activated carbon or an inorganic oxide.

(5) The method for producing 3-hydroxytetrahydrofuran according to any one of (2) to (4), in which a specific surface area of the carrier is not less than 50 m$^2$/g.

(6) The method for producing 3-hydroxytetrahydrofuran according to any one of (2) to (5), in which an average particle size of the carrier is 100 to 10000 μm.

(7) The method for producing 3-hydroxytetrahydrofuran according to any one of (2) to (6), in which an amount of the oxide supported on the carrier in the catalyst (in terms of a metal atom forming the oxide) is 0.01 to 50% by weight based on a total amount of the oxide and the carrier (100% by weight).

(8) The method for producing 3-hydroxytetrahydrofuran according to any one of (2) to (7), in which the catalyst further includes a metal other than a Group 6 element and a Group 7 element, the metal being supported on the carrier.

(9) The method for producing 3-hydroxytetrahydrofuran according to (8), in which the metal is at least one metal selected from the group consisting of palladium, platinum, iron, cobalt, nickel and copper.

(10) The method for producing 3-hydroxytetrahydrofuran according to (8) or (9), in which a ratio (molar ratio, in terms of metal) of the metal to the Group 6 element and Group 7 element forming the oxide in the catalyst [the metal/Group 6 element and Group 7 element] is 50/1 to 1/500.

(11) The method for producing 3-hydroxytetrahydrofuran according to any one of (4) to (10), in which the inorganic oxide is at least one inorganic oxide selected from the group consisting of titania, zirconia, magnesia, silica and alumina.

(12) The method for producing 3-hydroxytetrahydrofuran according to any one of (2) to (11), in which an average particle size of the catalyst is 100 to 10000 μm.

(13) The method for producing 3-hydroxytetrahydrofuran according to any one of (1) to (12), in which the reaction of 1,4-anhydroerythritol and hydrogen is allowed to proceed under the coexistence with a solid acid.

(14) The method for producing 3-hydroxytetrahydrofuran according to (13), in which an amount of the solid acid

(15) The method for producing 3-hydroxytetrahydrofuran according to any one of (1) to (14), in which a molar ratio of hydrogen to 1,4-anhydroerythritol subjected to the reaction [hydrogen (mol)/1,4-anhydroerythritol (mol)] is 1 to 100.
(16) The method for producing 3-hydroxytetrahydrofuran according to any one of (1) to (15), in which a reaction temperature of 1,4-anhydroerythritol and hydrogen in the reaction is 50 to 250° C.
(17) The method for producing 3-hydroxytetrahydrofuran according to any one of (1) to (16), in which a reaction time of 1,4-anhydroerythritol and hydrogen in the reaction is 0.1 to 100 hours.
(18) The method for producing 3-hydroxytetrahydrofuran according to any one of (1) to (17), in which a reaction pressure of 1,4-anhydroerythritol and hydrogen in the reaction (hydrogen pressure in the reaction of 1,4-anhydroerythritol and hydrogen) is 1 to 50 MPa.
(19) A hydrogenation reaction catalyst for 1,4-anhydroerythritol, in which the hydrogenation reaction catalyst is use for a reaction of 1,4-anhydroerythritol and hydrogen to produce 3-hydroxytetrahydrofuran, and includes a carrier and at least one oxide selected from the group consisting of an oxide of a Group 6 element and an oxide of a Group 7 element, the oxide being supported on the carrier.
(20) The hydrogenation reaction catalyst according to (19), in which the oxide is tungsten oxide.
(21) The hydrogenation reaction catalyst according to (19) or (20), in which the carrier is activated carbon or an inorganic oxide.
(22) The hydrogenation reaction catalyst according to any one of (19) to (21), in which a specific surface area of the carrier is not less than 50 m$^2$/g.
(23) The hydrogenation reaction catalyst according to any one of (19) to (22), in which an average particle size of the carrier is 100 to 10000 μm.
(24) The hydrogenation reaction catalyst according to any one of (19) to (23), in which an amount of the oxide supported on the carrier (in terms of a metal atom forming the oxide) is 0.01 to 50% by weight based on a total amount of the oxide and the carrier (100% by weight).
(25) The hydrogenation reaction catalyst according to any one of (19) to (24), further including a metal other than a Group 6 element and a Group 7 element, the metal being supported on the carrier.
(26) The hydrogenation reaction catalyst according to (25), in which the metal is at least one metal selected from the group consisting of palladium, platinum, iron, cobalt, nickel and copper.
(27) The hydrogenation reaction catalyst according to (25) or (26), in which a ratio (molar ratio, in terms of metal) of the metal to the Group 6 element and Group 7 element forming the oxide [the metal/Group 6 element and Group 7 element] is 50/1 to 1/500.
(28) The hydrogenation reaction catalyst according to any one of (21) to (27), in which the inorganic oxide is at least one inorganic oxide selected from the group consisting of titania, zirconia, magnesia, silica and alumina.
(29) The hydrogenation reaction catalyst according to any one of (19) to (28), in which an average particle size is 100 to 10000 μm.
(30) A method for producing 1,3-butane diol, including a step of reacting 3-hydroxytetrahydrofuran and hydrogen to produce 1,3-butane diol.
(31) The method for producing 1,3-butane diol according to (30), in which the step of reacting 3-hydroxytetrahydrofuran and hydrogen is allowed to proceed in the presence of a catalyst including a carrier and at least one metal selected from the group consisting of iridium, rhenium, ruthenium, molybdenum and tungsten, the metal supported on the carrier.
(32) The method for producing 1,3-butane diol according to (31), in which the catalyst includes iridium and rhenium as the metal.
(33) The method for producing 1,3-butane diol according to (31) or (32), in which the carrier is an inorganic oxide.
(34) The method for producing 1,3-butane diol according to (33), in which the inorganic oxide is at least one inorganic oxide selected from the group consisting of silica, magnesia, titania and alumina.
(35) The method for producing 1,3-butane diol according to any one of (31) to (34), in which a specific surface area of the carrier is not less than 50 m$^2$/g.
(36) The method for producing 1,3-butane diol according to any one of (31) to (35), in which an average particle size of the carrier is 100 to 10000 μm.
(37) The method for producing 1,3-butane diol according to any one of (31) to (36), in which an amount (total amount) (in terms of a metal atom) of at least one metal selected from the group consisting of iridium, rhenium, ruthenium, molybdenum and tungsten, supported on the carrier in the catalyst is 0.01 to 50% by weight based on a total amount of the metal and the carrier (100% by weight).
(38) The method for producing 1,3-butane diol according to any one of (31) to (37), in which a ratio (molar ratio, in terms of metal) of iridium to rhenium in the catalyst [iridium/rhenium] is 50/1 to 1/6.
(39) The method for producing 1,3-butane diol according to any one of (31) to (38), in which an average particle size of the catalyst is 100 to 10000 μm.
(40) The method for producing 1,3-butane diol according to any one of (30) to (39), in which the 3-hydroxytetrahydrofuran is 3-hydroxytetrahydrofuran produced by a reaction of 1,4-anhydroerythritol and hydrogen.
(41) The method for producing 1,3-butane diol according to any one of (30) to (40), in which a molar ratio of hydrogen to 3-hydroxytetrahydrofuran subjected to the reaction [hydrogen (mol)/3-hydroxytetrahydrofuran (mol)] is 1 to 100.
(42) The method for producing 1,3-butane diol according to any one of (30) to (41), in which a reaction temperature of 3-hydroxytetrahydrofuran and hydrogen in the reaction is 50 to 200° C.
(43) The method for producing 1,3-butane diol according to any one of (30) to (42), in which a reaction time of 3-hydroxytetrahydrofuran and hydrogen in the reaction is 0.1 to 100 hours.
(44) The method for producing 1,3-butane diol according to any one of (30) to (43), in which a reaction pressure of 3-hydroxytetrahydrofuran and hydrogen in the reaction (hydrogen pressure in the reaction of 3-hydroxytetrahydrofuran and hydrogen) is 1 to 50 MPa.
(45) The method for producing 1,3-butane diol according to any one of (30) to (44), further including, before the step, a step of reacting 1,4-anhydroerythritol and hydrogen to produce 3-hydroxytetrahydrofuran.
(46) A hydrogenation reaction catalyst for 3-hydroxytetrahydrofuran, in which the hydrogenation reaction catalyst is used for a reaction of 3-hydroxytetrahydrofuran and hydrogen to produce 1,3-butane diol, and includes a carrier and at least one metal selected from the group used is 0.1 to 50 parts by weight based on 100 parts by weight of 1,4-anhydroerythritol.

consisting of iridium, rhenium, ruthenium, molybdenum and tungsten, the metal being supported on the carrier.

(47) The hydrogenation reaction catalyst according to (46), including iridium and rhenium as the metal.

(48) The hydrogenation reaction catalyst according to (46) or (47), in which the carrier is an inorganic oxide.

(49) The hydrogenation reaction catalyst according to (48), in which the inorganic oxide is at least one inorganic oxide selected from the group consisting of silica, magnesia, titania and alumina.

(50) The hydrogenation reaction catalyst according to any one of (46) to (49), in which a specific surface area of the carrier is not less than 50 m$^2$/g.

(51) The hydrogenation reaction catalyst according to any one of (46) to (50), in which an average particle size of the carrier is 100 to 10000 μm.

(52) The hydrogenation reaction catalyst according to any one of (46) to (51), in which an amount (total amount) (in terms of a metal atom) of at least one metal selected from the group consisting of iridium, rhenium, ruthenium, molybdenum and tungsten, supported on the carrier is 0.01 to 50% by weight based on a total amount of the metal and the carrier (100% by weight).

(53) The hydrogenation reaction catalyst according to any one of (46) to (52), in which a ratio (molar ratio, in terms of metal) of iridium to rhenium [iridium/rhenium] is 50/1 to 1/6.

(54) The hydrogenation reaction catalyst according to any one of (46) to (53), in which an average particle size is 100 to 10000 μm.

Advantageous Effects of Invention

The method for producing 3-hydroxytetrahydrofuran of the present invention is a method for producing 3-hydroxytetrahydrofuran using, as a raw material, 1,4-anhydroerythritol, which can be derived from erythritol of biomass. Thus, the production method puts a small load on the environment and significantly contributes to building of a sustainable society. In addition, the production method can produce 3-hydroxytetrahydrofuran at a high selectivity and thus is advantageous also in terms of cost.

Similarly, the method for producing 1,3-butane diol of the present invention is a method for producing 1,3-butane diol using, as a raw material, 3-hydroxytetrahydrofuran that can be derived from, as a starting material, erythritol of biomass. Thus, the production method puts a small load on the environment and significantly contributes to building of a sustainable society. In addition, the production method can produce 1,3-butane diol at a high selectivity and thus is advantageous also in terms of cost.

BRIEF DESCRIPTION OF DRAWING

FIG. 1 is a flow diagram illustrating one example of hydrogenation reaction step A in the method for producing 3-hydroxytetrahydrofuran of the present invention or hydrogenation reaction step B in the method for producing 1,3-butane diol of the present invention, in the case of using a trickle bed reactor.

DESCRIPTION OF EMBODIMENTS

<Method for Producing 3-Hydroxytetrahydrofuran>

The method for producing 3-hydroxytetrahydrofuran of the present invention includes, as an essential step, a step of reacting 1,4-anhydroerythritol and hydrogen to produce 3-hydroxytetrahydrofuran (sometimes referred to as "hydrogenation reaction step A").

[1,4-Anhydroerythritol]

1,4-Anhydroerythritol (3,4-hydroxyoxolane) used as a raw material in hydrogenation reaction step A is a compound represented by the following formula (1). 1,4-Anhydroerythritol is a compound having a structure formed by dehydration condensation of hydroxyl groups at 1- and 4-positions of erythritol, as shown in the formula (1).

[Formula 1]

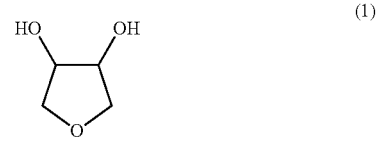

The 1,4-anhydroerythritol may be, for example, 1,4-anhydroerythritol produced by chemical synthesis or 1,4-anhydroerythritol derived from saccharides such as glucose by a fermentation technique, and is not particularly limited. Examples of the 1,4-anhydroerythritol derived by a fermentation technique include 1,4-anhydroerythritol produced by using, as a raw material, erythritol derived from saccharides such as glucose by a fermentation technique and subjecting the erythritol to an intramolecular dehydration reaction. The intramolecular dehydration reaction can be performed by a known or conventional method, is not particularly limited, and can be performed, for example, according to a method including a dehydration reaction step described later. Herein, as the 1,4-anhydroerythritol, 1,4-anhydroerythritol (unreacted 1,4-anhydroerythritol) can also be reused which is recovered from a reaction mixture obtained in hydrogenation reaction step A.

[Hydrogen]

Hydrogen (hydrogen gas) used in hydrogenation reaction step A can be used in the state of substantially only hydrogen, or can be used in the state of being diluted with an inert gas such as nitrogen, argon or helium. Hydrogen (unreacted hydrogen) that is recovered from the reaction mixture obtained through hydrogenation reaction step A can also be reused.

[Catalyst]

The reaction of 1,4-anhydroerythritol and hydrogen in hydrogenation reaction step A is preferably allowed to proceed in the presence of a catalyst (hydrogenation reaction catalyst for 1,4-anhydroerythritol, which is used for the reaction of 1,4-anhydroerythritol and hydrogen to produce 3-hydroxytetrahydrofuran). When the catalyst is used, the reaction tends to be accelerated to enhance the conversion of 1,4-anhydroerythritol and to enhance the selectivity of 3-hydroxytetrahydrofuran.

The catalyst is preferably a catalyst including a carrier and at least one oxide selected from the group consisting of an oxide of a Group 6 element and an oxide of a Group 7 element (sometimes simply referred to as "oxide"), the oxide being supported on the carrier (sometimes referred to as "catalyst (1) of the present invention"), particularly in view of the yield of 3-hydroxytetrahydrofuran. Examples of the Group 6 element include chromium (Cr), molybdenum (Mo), and tungsten (W). Examples of the Group 7 element include manganese (Mn), technetium (Tc), and rhenium (Re). Among them, tungsten is preferable as a metal forming the oxide (metal oxide) supported on the carrier in the catalyst (1) of the present invention.

As the carrier in the catalyst (1) of the present invention, a known or conventional carrier for use in a catalyst can be used and is not particularly limited, and examples thereof include inorganic carriers such as an inorganic oxide and activated carbon, and organic carriers such as an ion-exchange resin. Among them, activated carbon and an inorganic oxide are preferable in view of reaction activity.

As the activated carbon, known or conventional activated carbon can be used and is not particularly limited, and activated carbon obtained from any raw material such as vegetable, mineral and resin materials can also be used. As the activated carbon, a commercially available product such as "Vulcan XC72" (product name, manufactured by Cabot Corporation), "BP2000" (product name, manufactured by Cabot Corporation), "Shirasagi FAC-10" (product name, manufactured by Japan EnviroChemicals, Ltd.), "Shirasagi M" (product name, manufactured by Japan EnviroChemicals, Ltd.), "Shirasagi C" (product name, manufactured by Japan EnviroChemicals, Ltd.) or "Carboraffin" (product name, manufactured by Japan EnviroChemicals, Ltd.) can also be used.

As the inorganic oxide, a known or conventional inorganic oxide can be used and is not particularly limited, and examples thereof include titania ($TiO_2$), zirconia ($ZrO_2$), magnesia (MgO), silica ($SiO_2$) and alumina ($Al_2O_3$), and composites of two or more of these inorganic oxides (for example, zeolite). Among them, at least one inorganic oxide (inorganic metal oxide) selected from the group consisting of titania, zirconia, magnesia, silica and alumina is preferable in view of the yield of 3-hydroxytetrahydrofuran. As the inorganic oxide, a commercially available product such as "TIO-4" (product name) (titania, manufactured by Nippon Aerosil Co., Ltd.), "500A" (product name, manufactured by Ube Industries, Ltd.), "G-6" (product name) (silica, manufactured by Fuji Silysia Chemical Ltd.), "KHO-24" (product name) (alumina, manufactured by Sumitomo Chemical Co., Ltd.) or "Zirconia" (product name, manufactured by Wako Pure Chemical Industries, Ltd.) can also be used.

The specific surface area of the carrier is preferably, but not particularly limited to, not less than 50 $m^2/g$ (for example, 50 to 1500 $m^2/g$, preferably 100 to 1000 $m^2/g$) from the viewpoints that the oxide and other metal described later can be favorably dispersed, aggregation thereof can be suppressed, and the catalyst activity per unit weight can be enhanced. If the specific surface area of the carrier is less than the above range, the catalyst activity per unit weight tends to be reduced.

The average particle size of the carrier is preferably, but not particularly limited to, 100 to 10000 μm, more preferably 1000 to 10000 μm in view of reactivity and from the viewpoint that no excessive loss of pressure is caused in the case of performing the reaction in a continuous flowing system. In addition, the shape of the carrier may be any of powdery, granular, molded (molded article), and the like, and is not particularly limited.

The amount of the oxide supported on the carrier (in the case of a composite of two or more oxides, the total amount of such two or more oxides) (in terms of a metal atom (Group 6 element, Group 7 element) forming the oxide) is preferably, but not particularly limited to, 0.01 to 50% by weight, more preferably 0.01 to 20% by weight, further preferably 0.5 to 15% by weight, particularly preferably 1.0 to 10% by weight based on the total amount of the oxide and the carrier (100% by weight). If the amount of the oxide supported is less than 0.01% by weight, the conversion of 1,4-anhydroerythritol may be reduced. On the other hand, if the amount of the oxide supported is more than 50% by weight, the yield per unit metal may be uneconomically reduced, for example.

The method for supporting the oxide on the carrier is not particularly limited, and the oxide can be supported on the carrier by a known or conventional supporting method. Specifically, for example, the oxide can be supported on the carrier by impregnating the carrier with a solution containing a Group 6 element or a Group 7 element forming the oxide (for example, in the case of tungsten, an aqueous ammonium tungstate solution), then drying the resulting carrier and if necessary reducing the metal (reducing the metal (Group 6 element, Group 7 element)). Herein, the concentration of the solution containing a Group 6 element or a Group 7 element, and the number of applications of the impregnation and drying treatment of the carrier can be adjusted to thereby control the amount of the oxide supported. In addition, the temperature in impregnation of the carrier with the solution containing a Group 6 element or a Group 7 element, and the temperature in drying of the carrier impregnated with the solution are not particularly limited.

The temperature in further reduction of the metal (Group 6 element, Group 7 element) (firing temperature) after impregnation of the carrier with the solution containing a Group 6 element or a Group 7 element and drying of the carrier impregnated with the solution, is preferably, but not particularly limited to, 400 to 700° C., more preferably 450 to 550° C. in a hydrogen atmosphere. Herein, the reducing treatment is preferably performed in particular when a metal other than palladium and platinum is supported, as other metal described later, on the carrier, or such other metal is not supported on the carrier.

After the reducing treatment, passivation may be conducted if necessary. When passivation is performed, handling of the catalyst (1) of the present invention tends to become easy. Herein, passivation can be performed by a known or conventional method, and can be performed by, for example, but not particularly limited to, exposure to an oxygen atmosphere at around room temperature.

The catalyst (1) of the present invention preferably further includes a metal other than a Group 6 element and a Group 7 element (metal element: sometimes referred to as "other metal"), the metal being supported on the carrier. That is, the catalyst (1) of the present invention is preferably a catalyst including the carrier, the oxide supported on the carrier, and other metal supported on the carrier (accordingly, the oxide and other metal are supported on the carrier (the same carrier)). Other metal described above is not particularly limited as long as it is a metal other than a Group 6 element and a Group 7 element. However, it is preferably at least one metal selected from the group consisting of palladium (Pd), platinum (Pt), iron (Fe), cobalt (Co), nickel (Ni) and copper (Cu) in view of the yield of 3-hydroxytetrahydrofuran. When the catalyst (1) of the present invention includes such other metal supported on the carrier, the conversion of 1,4-anhydroerythritol and the selectivity of 3-hydroxytetrahydrofuran tend to be further enhanced.

The form of other metal described above included in the catalyst (1) of the present invention is not particularly limited, and examples thereof include the form in which other metal described above is included in the state of being supported on the carrier as a metal element, a metal salt, a metal oxide, a metal hydroxide or a metal complex.

The method for supporting other metal described above on the carrier is not particularly limited, and a known or conventional supporting method can be utilized. Specifically, for example, other metal described above can be supported by the same method as the method for supporting the oxide on the carrier, and a method including impregnating the carrier with a solution containing other metal described above, drying the resulting carrier, and then if necessary reducing such other metal (reducing other metal) is exemplified. More specifically, examples include a method including impregnating the carrier with the solution containing a Group 6 element or a Group 7 element, then drying the resulting carrier, thereafter further impregnating the dried carrier with the solution containing other metal described above, drying the resulting carrier, and then if necessary reducing such other metal. Herein, the temperature in impregnation of the carrier with the solution containing other metal described above, the temperature in drying of the carrier impregnated with the solution, and the temperature in reduction of other metal described above are not particularly limited. The reduction treatment after impregnation with the solution containing a Group 6 element or a Group 7 element, and the reduction treatment after impregnation with the solution containing other metal described above can also be simultaneously performed by, for example, impregnation with both the solutions and thereafter heating in a hydrogen atmosphere (for example, the heating temperature is preferably 400 to 700° C., more preferably 450 to 550° C.)

When the catalyst (1) of the present invention includes other metal described above supported on the carrier, the ratio (molar ratio, in terms of metal) of other metal described above (in the case of containing two or more, the total amount of such two or more) to the Group 6 element and Group 7 element forming the oxide (in the case of containing two or more, the total amount of such two or more) [other metal/Group 6 element and Group 7 element] is preferably, but not particularly limited to, 50/1 to 1/500, more preferably 50/1 to 1/6, further preferably 4/1 to 1/4. The amount of other metal described above used can be appropriately adjusted in the above range depending on the temperature and time where 1,4-anhydroerythritol and hydrogen are reacted.

The average particle size of the catalyst (1) of the present invention is preferably, but not particularly limited to, 100 to 10000 μm, more preferably 1000 to 10000 μm in view of reactivity and from the viewpoint that no excessive loss of pressure is caused in the case of performing the reaction in a continuous flowing system. In addition, the shape of the catalyst (1) of the present invention is not particularly limited, and examples thereof include powdery, granular and molded (molded article) shapes.

[Hydrogenation Reaction Step A]

Hydrogenation reaction step A in the method for producing 3-hydroxytetrahydrofuran of the present invention is preferably a step of reacting 1,4-anhydroerythritol and hydrogen in the presence of the catalyst (1) of the present invention to produce 1,3-hydroxytetrahydrofuran. The reaction of 1,4-anhydroerythritol and hydrogen may be a gas-solid two-phase reaction in which gaseous (gasified) 1,4-anhydroerythritol and hydrogen are reacted in the presence of the catalyst (1) of the present invention (solid), or may be a gas-liquid-solid three-phase reaction in which liquid 1,4-anhydroerythritol and hydrogen are reacted in the presence of the catalyst (1) of the present invention (solid). In particular, the above reaction is preferably allowed to proceed in a gas-liquid-solid three-phase system from the viewpoint of inhibiting a compound having 3 or less carbon atoms from being produced by cleavage of a carbon-carbon bond.

More specifically, the reaction of 1,4-anhydroerythritol and hydrogen in hydrogenation reaction step A can be allowed to proceed by, for example, enclosing a raw material liquid including 1,4-anhydroerythritol as an essential component, and hydrogen in a reactor, and heating the resultant preferably in the presence of the catalyst (1) of the present invention. Herein, the catalyst (1) of the present invention in hydrogenation reaction step A can be used singly or in combination of two or more.

The raw material liquid may contain, in addition to 1,4-anhydroerythritol, a solvent such as water or an organic solvent, or substantially no solvent. The organic solvent is not particularly limited, and examples thereof include alcohols such as methanol, ethanol, isopropanol, n-butanol and 2-butanol, and dimethylsulfoxide (DMSO), dimethylformamide (DMF), dimethylacetamide (DMAc) and 1,4-dioxane. In the raw material liquid, among them, 1,4-dioxane is preferable from the viewpoint that the reactivity of 1,4-anhydroerythritol and hydrogen is excellent. As the raw material liquid, a reaction mixture obtained by an intramolecular dehydration reaction of erythritol in a dehydration reaction step described later, or a solution obtained by, if necessary, removing an acid catalyst or the like from the reaction mixture can be used. Herein, the solvent can be used singly or in combination of two or more.

The concentration of 1,4-anhydroerythritol in the raw material liquid (content of 1,4-anhydroerythritol in 100% by weight of the raw material liquid) is preferably, but not particularly limited to, 5 to 98% by weight, more preferably 8 to 90% by weight, further preferably 10 to 90% by weight, particularly preferably 15 to 80% by weight. If the concentration of 1,4-anhydroerythritol is less than 5% by weight, the reaction rate (conversion) of 1,4-anhydroerythritol may be reduced. On the other hand, if the concentration of 1,4-anhydroerythritol is more than 98% by weight, an increase in viscosity may be caused to make operations complicated.

The reaction of 1,4-anhydroerythritol and hydrogen may be allowed to proceed under the coexistence with a solid acid. That is, the raw material liquid may contain a solid acid in addition to 1,4-anhydroerythritol and the solvent described above. Herein, the solid acid is a solid exhibiting characteristics of Bronsted acid and/or Lewis acid (any one or both of Bronsted acid and Lewis acid) and having a Hammett acidity function ($H_0$) of 6.8 or less. As the solid acid, a known or conventional solid acid can be used and is not particularly limited, and examples include a solid in which inorganic acids or organic acids (for example, organic sulfonic acids) are supported on the carrier (for example, silica, alumina, zeolite, and silica-alumina); a crystalline metal silicate (for example, H-ZSM-5 that is proton type zeolite) such as gallium silicate, aluminosilicate and borosilicate; a heteropoly acid or a salt thereof; a solid in which a heteropoly acid or a salt thereof is supported on a carrier (for example, silica or alumina); a metal oxide such as zirconium oxide ($ZrO_2$) and titanium oxide ($TiO_2$); and a polymer having an acid group such as a carboxyl group or a sulfonic acid group (for example, a cation-exchange resin). As the solid acid, a commercially available product can also be utilized. The reaction of 1,4-anhydroerythritol and hydrogen can be promoted by allowing the reaction to proceed under the coexistence with the solid acid. Herein, the solid acid can be used singly or in combination of two or more.

The amount of the solid acid used (content) is preferably, but not particularly limited to, 0.1 to 50 parts by weight, more preferably 1 to 20 parts by weight based on 100 parts by weight of 1,4-anhydroerythritol. In the case of the coexistence with the solid acid, a step of removing the solid acid by filtration after completion of the reaction is preferably performed.

In the above reaction, other components may coexist as long as the effects of the present invention are not impaired. That is, the raw material liquid may contain other components (for example, alcohols) as long as the effects of the present invention are not impaired. While the raw material liquid may include, for example, impurities (for example, a long-chain fatty acid, a metal salt, a sulfur-containing compound such as thiol or thioether, or a nitrogen-containing compound such as amine) derived from a raw material of 1,4-anhydroerythritol (erythritol, a raw material of the erythritol, or the like), such impurities may cause the catalyst to be degraded and thus is preferably removed from the raw material liquid by a known or conventional method (for example, distillation, adsorption, ion exchange, crystallization or extraction).

The raw material liquid is not particularly limited, and can be obtained by mixing 1,4-anhydroerythritol, and if necessary the solvent, the solid acid and other components. A known or conventional stirrer or the like can be used for such mixing.

The molar ratio of hydrogen to 1,4-anhydroerythritol subjected to the above reaction (reaction of 1,4-anhydroerythritol and hydrogen) [hydrogen (mol)/1,4-anhydroerythritol (mol)] is preferably, but not particularly limited to, 1 to 100, more preferably 1 to 50, further preferably 1 to 30. If the molar ratio is less than 1, the reaction rate (conversion) of 1,4-anhydroerythritol may be reduced. On the other hand, if the molar ratio is more than 100, the utility cost for recovery of unreacted hydrogen tends to be increased.

The reaction temperature of 1,4-anhydroerythritol and hydrogen in the above reaction is preferably, but not particularly limited to, 50 to 250° C., more preferably 60 to 220° C., further preferably 70 to 200° C. If the reaction temperature is lower than 50° C., the reaction rate (conversion) of 1,4-anhydroerythritol may be reduced. On the other hand, if the reaction temperature is higher than 250° C., decomposition (for example, cleavage of a carbon-carbon bond) of 1,4-anhydroerythritol is easily caused, and the yield of 3-hydroxytetrahydrofuran may be reduced. Herein, the reaction temperature may be controlled in a constant manner (substantially constant), or may be controlled in a stepwise or continuously changing manner, in the reaction.

The reaction time of 1,4-anhydroerythritol and hydrogen in the above reaction is preferably, but not particularly limited to, 0.1 to 100 hours, more preferably 0.2 to 80 hours, further preferably 0.5 to 60 hours. If the reaction time is less than 0.1 hours, the reaction rate (conversion) of 1,4-anhydroerythritol may not be sufficiently increased. On the other hand, if the reaction time is more than 100 hours, the selectivity of 3-hydroxytetrahydrofuran may be reduced.

The reaction pressure of 1,4-anhydroerythritol and hydrogen in the above reaction (hydrogen pressure in the reaction of 1,4-anhydroerythritol and hydrogen) is preferably, but not particularly limited to, 1 to 50 MPa, more preferably 3 to 30 MPa, further preferably 5 to 15 MPa. If the reaction pressure is less than 1 MPa, the reaction rate (conversion) of 1,4-anhydroerythritol may be reduced. On the other hand, if the reaction pressure is more than 50 MPa, the reactor is required to have a high pressure resistance and thus the production cost tends to be higher.

The above reaction can be performed by any system such as a batchwise system, a semi-batchwise system or a continuous flowing system. When the amount of 3-hydroxytetrahydrofuran obtained from a predetermined amount of 1,4-anhydroerythritol is aimed to be increased, a process can be adopted in which the unreacted 1,4-anhydroerythritol after completion of the reaction is separated and recovered for recycling. By adopting this recycle process, the amount of 3-hydroxytetrahydrofuran produced can be increased using a predetermined amount of 1,4-anhydroerythritol.

In hydrogenation reaction step A, a known or conventional reactor can be used as the reactor, and for example, a batchwise reactor, a fluid bed reactor, a fixed bed reactor or the like can be used. As the fixed bed reactor, for example, a trickle bed reactor can be used. The trickle bed reactor is a reactor (fixed bed continuous reaction apparatus) having a catalytic packed bed packed with a solid catalyst therein, in which both of a liquid (in hydrogenation reaction step A, for example, the raw material liquid) and a gas (in hydrogenation reaction step A, hydrogen) are allowed to flow through the catalytic packed bed in downflow (gas-liquid downward concurrent flow) from the upward of the reactor.

FIG. 1 is a flow diagram illustrating one example of hydrogenation reaction step A in the method for producing 3-hydroxytetrahydrofuran in the case of using the trickle bed reactor. In FIG. 1, reference numeral 1 denotes a reactor (trickle bed reactor), reference numeral 2 denotes a raw material liquid supply line, and reference numeral 3 denotes a hydrogen supply line. In addition, reference numeral 4 denotes a reaction mixture-ejecting line, reference numeral 5 denotes a high-pressure gas-liquid separator, and reference numeral 6 denotes a hydrogen recycle line. Hereinafter, the method for producing 3-hydroxytetrahydrofuran using the trickle bed reactor is simply described with reference to FIG. 1.

First, the raw material liquid and hydrogen are continuously supplied from above the trickle bed reactor 1, and thereafter 1,4-anhydroerythritol and hydrogen in the raw material liquid are reacted in the reactor in the presence of a catalyst (the catalyst (1) of the present invention) in a catalytic packed bed, to produce 3-hydroxytetrahydrofuran (reaction product). Then, a reaction mixture including the 3-hydroxytetrahydrofuran is continuously taken out through the reaction mixture-ejecting line 4 located below the trickle bed reactor 1. Thereafter, hydrogen is if necessary separated from the reaction mixture by the high-pressure gas-liquid separator 5, and 3-hydroxytetrahydrofuran is then purified and isolated in a purification step. Hydrogen separated by the high-pressure gas-liquid separator 5 can also be supplied through the hydrogen recycle line 6 to the trickle bed reactor 1 again and recycled in the reaction.

When the trickle bed reactor is adopted as the reactor, the reaction can be allowed to proceed in a gas-liquid-solid three-phase system without gasifying 1,4-anhydroerythritol as the raw material, and thus such a reactor is advantageous in terms of cost. In addition, since the raw material liquid including 1,4-anhydroerythritol flows downward in the trickle bed reactor while forming a thin film on the surface of the catalyst, the distance from the interface between the raw material liquid and hydrogen (gas-liquid interface) to the surface of the catalyst can be short to allow hydrogen dissolved in the raw material liquid to be easily diffused in the surface of the catalyst, effectively producing 3-hydroxytetrahydrofuran. Moreover, a process for separating the catalyst from the reaction product of 1,4-anhydroerythritol and hydrogen is also not required and a regeneration treatment of the catalyst is also easily performed. Therefore a production process is simple and excellent in terms of cost.

Herein, the material, shape and size (for example, column diameter and column length) of the trickle bed reactor are not particularly limited, and can be appropriately selected depending on the scale and the like of the reaction with reference to a known or conventional trickle bed reactor. The trickle bed reactor may be configured from a single reaction tube, or may be a multistage reactor configured from a plurality of reaction tubes. When the trickle bed reactor is a multistage reactor, the number of reaction tubes can be appropriately selected and is not particularly limited. When the trickle bed reactor is a multistage reactor, the reactor may be a reactor in which a plurality of reaction tubes are arranged in series or may be a reactor in which a plurality of reaction tubes are arranged in parallel.

Furthermore, the catalytic packed bed in the trickle bed reactor may be disposed with being divided (separated) at 2 or more positions in order to suppress overheating by reaction heat, for example.

In hydrogenation reaction step A, 3-hydroxytetrahydrofuran is produced as a reaction product of the reaction of 1,4-anhydroerythritol and hydrogen. 3-Hydroxytetrahydrofuran is represented by the following formula (2).

[Formula 2]

(2)

The method for producing 3-hydroxytetrahydrofuran of the present invention may also include if necessary a step other than hydrogenation reaction step A. Examples of such other step include a step of preparing and purifying the raw material liquid before supplying the raw material liquid and hydrogen to the reactor, and a step of separating and purifying the reaction mixture (for example, mixture of 1,4-anhydroerythritol, hydrogen, and a product such as 3-hydroxytetrahydrofuran) discharged (flown out) from the reactor. Herein, such steps may be performed in a different line from that of hydrogenation reaction step A, or may be performed (in-line) as a series of steps including hydrogenation reaction step A.

The method for producing 3-hydroxytetrahydrofuran of the present invention may include, for example, a step of producing 1,4-anhydroerythritol as the raw material in step A, before hydrogenation reaction step A. The step of producing 1,4-anhydroerythritol is particularly preferably a step of producing 1,4-anhydroerythritol by an intramolecular dehydration reaction of erythritol (sometimes referred to as "dehydration reaction step").

[Dehydration Reaction Step]

The intramolecular dehydration reaction of erythritol in the dehydration reaction step can be performed by a well-known method, and is not particularly limited. The reaction can be allowed to proceed by, for example, heating erythritol in the presence of an acid catalyst. Herein, the dehydration reaction step may be performed in a different line from that of hydrogenation reaction step A, or may be performed as a series of steps including hydrogenation reaction step A.

Erythritol for use as the raw material in the dehydration reaction step is not particularly limited, and may be erythritol produced by chemical synthesis, or erythritol derived from saccharides such as glucose by a fermentation technique. In particular, erythritol derived from saccharides such as glucose by a fermentation technique is preferably used from the viewpoint of a reduction in load on the environment. Erythritol (unreacted erythritol) recovered from the reaction mixture obtained in the dehydration reaction step can also be reused.

As the acid catalyst used in the dehydration reaction step, a known or conventional acid can be used and is not particularly limited, and examples include inorganic acids such as hydrochloric acid, sulfuric acid, nitric acid, phosphoric acid, polyphosphoric acid, metaphosphoric acid, condensed phosphoric acid, hydrobromic acid, perchloric acid, hypochlorous acid and chlorous acid; organic acids such as p-toluenesulfonic acid, trichloroacetic acid, trifluoroacetic acid and trifluoromethanesulfonic acid; and solid acids such as a cation-exchange resin, zeolite, silica alumina and heteropoly acid (for example, phosphomolybdic acid). Among them, solid acids are preferable because of being easily separated from the product and the like to be regenerated. Herein, as the acid catalyst, a commercially available product can also be used and examples of commercially available products of solid acids include "Amberlyst" (product name, manufactured by Dow Chemical Company) and "Nafion" (product name, manufactured by Du Pont Kabushiki Kaisha). Herein, such acids (acid catalyst) can be used singly or in combination of two or more.

The reaction (intramolecular dehydration reaction) can be allowed to proceed in the absence of a solvent or in the presence of a solvent. Examples of the solvent include water; alcohols such as methanol, ethanol, isopropanol and n-butanol; and highly polar organic solvents such as dimethylsulfoxide (DMSO), dimethylformamide (DMF) and dimethylacetamide (DMAc). Among them, at least water is preferably contained in the solvent because of being excellent in reactivity, and being easy in handling and disposal. Herein, the solvent can be used singly or in combination of two or more.

The reaction temperature (heating temperature) of the reaction (intramolecular dehydration reaction) is preferably, but not particularly limited to, 40 to 240° C., more preferably 80 to 200° C., further preferably 120 to 180° C. When the reaction temperature is controlled in the above range, the intramolecular dehydration reaction of erythritol can be more effectively allowed to proceed. Herein, the reaction temperature may be controlled in a constant manner (substantially constant), or may be controlled in a stepwise or continuously changing manner, in the reaction.

The time (reaction time) of the reaction (intramolecular dehydration reaction) is preferably, but not particularly limited to, 1 to 100 hours, more preferably 2 to 50 hours, further preferably 3 to 30 hours. If the reaction time is less than 1 hour, the reaction rate (conversion) of erythritol may not be sufficiently increased. On the other hand, if the reaction time is more than 100 hours, there may be a disadvantage in terms of cost.

The reaction (intramolecular dehydration reaction) can be performed in any of an air atmosphere and an atmosphere of an inert gas such as nitrogen or argon. The reaction is preferably performed in an inert gas atmosphere in particular from the viewpoint of an enhancement in the selectivity of 1,4-anhydroerythritol. The reaction (intramolecular dehydration reaction) can be performed under any of ordinary pressure, increased pressure and reduced pressure. The reaction is preferably performed under increased pressure in particular from the viewpoint of an enhancement in the conversion of erythritol. For example, when water is used as the solvent, the reaction temperature can be increased to 100° C. or higher by performing the reaction under increased pressure, effectively increasing the conversion of erythritol.

The reaction (intramolecular dehydration reaction) can be performed in any system such as a batchwise system, a semi-batchwise system or a continuous flowing system.

In the dehydration reaction step, 1,4-anhydroerythritol is produced. While 1,4-anhydroerythritol thus obtained is then used as the raw material in hydrogenation reaction step A, it can also be used after being isolated from the reaction mixture obtained in the dehydration reaction step by a known or conventional method (for example, distillation, adsorption, ion exchange, crystallization or extraction), or can be used without being isolated from the reaction mixture (if necessary, after the acid catalyst and the like are removed).

<Method for Producing 1,3-Butane Diol>

The method for producing 1,3-butane diol of the present invention includes a step of reacting 3-hydroxytetrahydrofuran and hydrogen to produce 1,3-butane diol (sometimes referred to as "hydrogenation reaction step B"), as an essential step.

[3-Hydroxytetrahydrofuran]

In hydrogenation reaction step B, 3-hydroxytetrahydrofuran used as the raw material can be, for example, one obtained by the method for producing 3-hydroxytetrahydrofuran of the present invention (method including hydrogenation reaction step A, or the dehydration reaction step and hydrogenation reaction step A), or one obtained by other method. In particular, 3-hydroxytetrahydrofuran obtained by the former method (3-hydroxytetrahydrofuran obtained by the reaction of 1,4-anhydroerythritol and hydrogen) can be used to thereby contribute to a reduction in load on the environment.

[Hydrogen]

Hydrogen (hydrogen gas) used in hydrogenation reaction step B can be used in the state of substantially only hydrogen, or can be used in the state of being diluted with an inert gas such as nitrogen, argon or helium, or the like. Hydrogen (unreacted hydrogen) that is recovered from the reaction mixture obtained through hydrogenation reaction step B can also be reused.

[Catalyst]

The reaction of 3-hydroxytetrahydrofuran and hydrogen in hydrogenation reaction step B is preferably allowed to proceed in the presence of a catalyst (hydrogenation reaction catalyst for 3-hydroxytetrahydrofuran, which is used for the reaction of 3-hydroxytetrahydrofuran and hydrogen to produce 1,3-butane diol). When the catalyst is used, the reaction tends to be accelerated to enhance the conversion of 3-hydroxytetrahydrofuran and to enhance the selectivity of 1,3-butane diol.

The catalyst is preferably a catalyst including a carrier and at least one metal selected from the group consisting of iridium (Ir), rhenium (Re), ruthenium (Ru), molybdenum (Mo) and tungsten (W) (metal component; hereinafter, sometimes referred to as "iridium and/or the like") supported on the carrier (sometimes referred to as "catalyst (2) of the present invention"), particularly in view of the yield of 1,3-butane diol. The form (state) of iridium and/or the like in the catalyst (2) of the present invention is not particularly limited as long as iridium and/or the like is supported on the carrier. Examples of the form of iridium and/or the like include a metal element, a metal salt, a metal oxide, a metal hydroxide and a metal complex. In particular, the catalyst (2) of the present invention preferably includes at least iridium or rhenium supported on the carrier, particularly preferably includes at least iridium and rhenium supported on the carrier in view of the reactivity of the reaction of 3-hydroxytetrahydrofuran and hydrogen.

As the carrier, a known or conventional carrier for use as the carrier of a catalyst can be used and is not particularly limited, and examples include inorganic carriers such as an inorganic oxide and activated carbon, and organic carriers such as an ion-exchange resin. As the carrier, among them, an inorganic oxide is preferable from the viewpoint of being excellent in reaction activity. Examples of the inorganic oxide include silica ($SiO_2$), titania ($TiO_2$), zirconia ($ZrO_2$), alumina ($Al_2O_3$) and magnesia (MgO), and composites of two or more of these inorganic oxides (for example, zeolite). Among the inorganic oxides, at least one inorganic oxide selected from the group consisting of silica, magnesia, titania and alumina is particularly preferable from the viewpoint of being excellent in reaction activity. Herein, the carrier in the catalyst (2) of the present invention can be used singly or in combination of two or more.

The specific surface area of the carrier is preferably, but not particularly limited to, not less than 50 $m^2/g$ (for example, 50 to 1500 $m^2/g$, preferably 100 to 1000 $m^2/g$) from the viewpoints that iridium and/or the like can be highly dispersed and arranged, such metal(s) can be inhibited from aggregating, and the catalyst activity per unit weight can be enhanced. If the specific surface area of the carrier is less than the above range, the catalyst activity per unit weight tends to be reduced.

The average particle size of the carrier is preferably, but not particularly limited to, 100 to 10000 μm, more preferably 1000 to 10000 μm in view of reactivity and from the viewpoint that no excessive loss of pressure is caused in the case of performing the reaction in a continuous flowing system. The shape of the carrier may be any of powdery, granular, molded (molded article), and the like, and is not particularly limited.

The amount of iridium and/or the like supported on the carrier (in the case of containing two or more metals, the total amount of such two or more) (in terms of a metal atom) is preferably, but not particularly limited to, 0.01 to 50% by weight, more preferably 0.01 to 20% by weight, further preferably 0.5 to 15% by weight, particularly preferably 1.0 to 10% by weight based on the total amount of iridium and/or the like, and the carrier (100% by weight). If the amount of iridium and/or the like supported is less than 0.01% by weight, the conversion of 3-hydroxytetrahydrofuran tends to be reduced. On the other hand, if the amount of iridium and/or the like supported is more than 50% by weight, there may be an economic disadvantage.

The method for supporting iridium and/or the like (in particular, iridium) on the carrier is not particularly limited, and a known or conventional supporting method can be utilized. Specifically, for example, iridium and/or the like can be supported by a method including impregnating the carrier with a solution containing iridium and/or the like (for example, in the case of iridium, an aqueous chloroiridic acid solution), thereafter drying and then firing the resulting carrier. Herein, the concentration of the solution containing iridium and/or the like, and the number of applications of the impregnation and drying treatment of the carrier can be adjusted to thereby control the amount of iridium and/or the like supported. In addition, the temperature in impregnation of the carrier with the solution containing iridium and/or the like, and the temperature in drying of the carrier impregnated with the solution are not particularly limited. When two or more of iridium and/or the like are supported on the carrier, two or more solutions containing iridium and/or the like can be used to support them on the carrier by the above method.

The temperature in firing of the carrier (firing temperature) after impregnation of the carrier with the solution containing iridium and/or the like and drying of the carrier impregnated with the solution, is not particularly limited, and is, for example, preferably 400 to 700° C., more preferably 450 to 550° C. in the air. In addition, the atmosphere in firing is not limited to the air as described above, and such firing can be conducted in, for example, an atmosphere of an inert gas such as nitrogen or argon, or an atmosphere of a reducing gas such as hydrogen.

In particular, when the catalyst (2) of the present invention contains at least iridium and rhenium supported on the carrier, the ratio (molar ratio, in terms of metal) of iridium to rhenium [iridium/rhenium] is preferably, but not particularly limited to, 50/1 to 1/6, more preferably 4/1 to 1/4, further preferably 3/1 to 1/3 in view of the conversion of 3-hydroxytetrahydrofuran.

The average particle size of the catalyst (2) of the present invention is preferably, but not particularly limited to, 100 to 10000 μm, more preferably 1000 to 10000 μm in view of reactivity and from the viewpoint that no excessive loss of pressure is caused in the case of performing the reaction in a continuous flowing system. In addition, the shape of the catalyst (2) of the present invention is not particularly limited, and examples include powdery, granular and molded (molded article) shapes.

[Hydrogenation Reaction Step B]

Hydrogenation reaction step B in the method for producing 1,3-butane diol of the present invention is preferably a step of reacting 3-hydroxytetrahydrofuran and hydrogen in the presence of the catalyst (2) of the present invention to produce 1,3-butane diol. The reaction of 3-hydroxytetrahydrofuran and hydrogen may be a gas-solid two-phase reaction in which gaseous (gasified) 1,3-hydroxytetrahydrofuran and hydrogen are reacted in the presence of the catalyst (2) of the present invention (solid), or a gas-liquid-solid three-phase reaction in which liquid 3-hydroxytetrahydrofuran and hydrogen are reacted in the presence of the catalyst (2) of the present invention (solid). In particular, the above reaction is preferably allowed to proceed in a gas-liquid-solid three-phase system from the viewpoint of inhibiting a compound having 3 or less carbon atoms from being produced by cleavage of a carbon-carbon bond.

More specifically, the reaction of 3-hydroxytetrahydrofuran and hydrogen in hydrogenation reaction step B can be allowed to proceed by, for example, enclosing a raw material liquid including 3-hydroxytetrahydrofuran as an essential component, and hydrogen in a reactor, and heating the resultant in the presence of the catalyst (2) of the present invention. Herein, the catalyst (2) of the present invention in hydrogenation reaction step B can be used singly or in combination of two or more.

The raw material liquid may contain, in addition to 3-hydroxytetrahydrofuran, a solvent such as water or an organic solvent, or substantially no solvent. The organic solvent is not particularly limited, and examples thereof include alcohols such as methanol, ethanol, isopropanol, n-butanol and 2-butanol, and highly polar organic solvents such as dimethylsulfoxide (DMSO), dimethylformamide (DMF) and dimethylacetamide (DMAc). Among them, at least water is preferably contained as the solvent in the raw material liquid because of being excellent in reactivity and being easy in handling and disposal. Herein, the solvent can be used singly or in combination of two or more.

The concentration of 3-hydroxytetrahydrofuran in the raw material liquid (content of 3-hydroxytetrahydrofuran based on 100% by weight of the raw material liquid) is preferably, but not particularly limited to, 5 to 98% by weight, more preferably 8 to 90% by weight, further preferably 10 to 90% by weight, particularly preferably 15 to 80% by weight. If the concentration of 3-hydroxytetrahydrofuran is less than 5% by weight, the reaction rate (conversion) of 3-hydroxytetrahydrofuran may be reduced. On the other hand, if the concentration of 3-hydroxytetrahydrofuran is more than 98% by weight, an increase in viscosity may be caused to make operations complicated.

The reaction of 3-hydroxytetrahydrofuran and hydrogen may be allowed to proceed under the coexistence with an acid. That is, the raw material liquid may contain an acid in addition to 3-hydroxytetrahydrofuran and the solvent described above. The acid is not particularly limited, and examples thereof include known or conventional acids such as sulfuric acid, phosphoric acid and trifluoromethanesulfonic acid. By allowing the reaction to proceed under the coexistence with the acid, the reaction of 3-hydroxytetrahydrofuran and hydrogen can be accelerated. Herein, the acid can be used singly or in combination of two or more.

The amount of the acid used (content) is preferably, but not particularly limited to, 0.1 to 10 mol times, more preferably 0.5 to 3 mol times as much as the amount of iridium and/or the like contained in the catalyst (in terms of metal, in the case of containing two or more metals, the total amount of such two or more). In the case of the coexistence with the acid, it is preferable to perform a step of neutralizing the acid after completion of the reaction.

Other components may coexist in the above reaction as long as the effects of the present invention are not impaired. That is, the raw material liquid may contain other components (for example, alcohols) as long as the effects of the present invention are not impaired. While the raw material liquid may include, for example, impurities (for example, a long-chain fatty acid, a metal salt, a sulfur-containing compound such as thiol or thioether, or a nitrogen-containing compound such as amine) derived from a raw material of 3-hydroxytetrahydrofuran (erythritol, 1,4-anhydroerythritol, raw materials thereof, or the like), such impurities may cause the catalyst to be degraded and thus is preferably removed from the raw material liquid by a known or conventional method (for example, distillation, adsorption, ion exchange, crystallization or extraction).

The raw material liquid is not particularly limited, and can be obtained by uniformly mixing 3-hydroxytetrahydrofuran, and if necessary the solvent, the acid and other components. A known or conventional stirrer or the like can be used for such mixing.

The molar ratio of hydrogen to 3-hydroxytetrahydrofuran subjected to the reaction (reaction of 3-hydroxytetrahydrofuran and hydrogen) [hydrogen (mol)/3-hydroxytetrahydrofuran (mol)] is preferably, but not particularly limited to, 1 to 100, more preferably 1.5 to 50, further preferably 2 to 30. If the molar ratio is less than 1, the reaction rate (conversion) of 3-hydroxytetrahydrofuran may be reduced. On the other hand, if the molar ratio is more than 100, the utility cost for recovery of unreacted hydrogen tends to be increased.

The reaction temperature of 3-hydroxytetrahydrofuran and hydrogen in the above reaction is preferably, but not particularly limited to, 50 to 200° C., more preferably 60 to 150° C., further preferably 70 to 130° C. If the reaction temperature is lower than 50° C., the reaction rate (conversion) of 3-hydroxytetrahydrofuran may be reduced. On the other hand, if the reaction temperature is higher than 200° C., decomposition (for example, cleavage of a carbon-carbon bond) of 3-hydroxytetrahydrofuran is easily caused, and the selectivity of 1,3-butane diol may be reduced.

Herein, the reaction temperature may be controlled in a constant manner (substantially constant), or may be controlled in a stepwise or continuously changing manner, in the reaction.

The reaction time of 3-hydroxytetrahydrofuran and hydrogen in the above reaction is preferably, but not particularly limited to, 0.1 to 100 hours, more preferably 0.2 to 10 hours, further preferably 0.5 to 8 hours. If the reaction time is less than 0.1 hours, the reaction rate (conversion) of 3-hydroxytetrahydrofuran may not be sufficiently increased. On the other hand, if the reaction time is more than 100 hours, the selectivity of 1,3-butane diol may be reduced.

The reaction pressure of 3-hydroxytetrahydrofuran and hydrogen in the above reaction (hydrogen pressure in the reaction of 3-hydroxytetrahydrofuran and hydrogen) is preferably, but not particularly limited to, 1 to 50 MPa, more preferably 3 to 30 MPa, further preferably 5 to 15 MPa. If the reaction pressure is less than 1 MPa, the reaction rate (conversion) of 3-hydroxytetrahydrofuran may be reduced. On the other hand, if the reaction pressure is more than 50 MPa, the reactor is required to have a high pressure resistance and thus the production cost tends to be higher.

The above reaction can be performed by any system such as a batchwise system, a semi-batchwise system or a continuous flowing system. When the amount of 1,3-butane diol obtained from a predetermined amount of 3-hydroxytetrahydrofuran is aimed to be increased, a process may be adopted in which the unreacted 3-hydroxytetrahydrofuran after completion of the reaction is separated and recovered for recycling. By adopting this recycle process, the amount of 1,3-butane diol produced can be increased using a predetermined amount of 3-hydroxytetrahydrofuran.

In hydrogenation reaction step B, a known or conventional reactor can be used as the reactor, and for example, a batchwise reactor, a fluid bed reactor, a fixed bed reactor or the like can be used. As the fixed bed reactor, for example, a trickle bed reactor illustrated in FIG. 1 can also be used. FIG. 1 is also a flow diagram illustrating one example of hydrogenation reaction step B in the method for producing 1,3-butane diol, in the case of using the trickle bed reactor. Hereinafter, the method for producing 1,3-butane diol using the trickle bed reactor is simply described with reference to FIG. 1.

First, the raw material liquid and hydrogen are continuously supplied from above the trickle bed reactor 1, and thereafter 3-hydroxytetrahydrofuran and hydrogen in the raw material liquid are reacted in the reactor in the presence of a catalyst in a catalytic packed bed, to produce 1,3-butane diol (reaction product). Then, a reaction mixture including the 1,3-butane diol is continuously taken out through the reaction mixture-ejecting line 4 located below the trickle bed reactor 1. Thereafter, hydrogen is if necessary separated from the reaction mixture by the high-pressure gas-liquid separator 5, and 1,3-butane diol is then purified and isolated in a purification step. Hydrogen separated by the high-pressure gas-liquid separator 5 can also be supplied through the hydrogen recycle line 6 to the trickle bed reactor 1 again and recycled in the reaction.

When the trickle bed reactor is adopted as the reactor, the reaction can be allowed to proceed in a gas-liquid-solid three-phase system without gasifying 3-hydroxytetrahydrofuran being the raw material, and thus such a reactor is advantageous in terms of cost. In addition, since the raw material liquid including 3-hydroxytetrahydrofuran flows downward in the trickle bed reactor while forming a thin film on the surface of the catalyst, the distance from the interface between the raw material liquid and hydrogen (gas-liquid interface) to the surface of the catalyst can be short to allow hydrogen dissolved in the raw material liquid to be easily diffused in the surface of the catalyst, effectively producing 1,3-butane diol. Moreover, a process for separating the catalyst from the reaction product of 3-hydroxytetrahydrofuran and hydrogen is also not required and a regeneration treatment of the catalyst is also easily performed. Therefore a production process is simple and excellent in terms of cost.

Herein, the material, shape and size (for example, column diameter and column length) of the trickle bed reactor are not particularly limited, and can be appropriately selected depending on the scale and the like of the reaction with reference to a known or conventional trickle bed reactor. The trickle bed reactor may be configured from a single reaction tube, or may be a multistage reactor configured from a plurality of reaction tubes. When the trickle bed reactor is a multistage reactor, the number of reaction tubes can be appropriately selected and is not particularly limited. When the trickle bed reactor is a multistage reactor, the reactor may be a reactor in which a plurality of reaction tubes are arranged in series or may be a reactor in which a plurality of reaction tubes are arranged in parallel.

Furthermore, the catalytic packed bed in the trickle bed reactor may be disposed with being divided (separated) at 2 or more positions in order to suppress overheating by reaction heat, for example.

The method for producing 1,3-butane diol of the present invention may also include if necessary a step other than hydrogenation reaction step B. Examples of such other step include a step of preparing and purifying the raw material liquid before supplying the raw material liquid and hydrogen to the reactor, and a step of separating and purifying the reaction mixture (for example, mixture of 3-hydroxytetrahydrofuran, hydrogen, 1,3-butane diol, and the like) discharged (flown out) from the reactor. Herein, such steps may be performed in a different line from that of hydrogenation reaction step B, or may be performed (in-line) as a series of steps including hydrogenation reaction step B.

The method for producing 1,3-butane diol of the present invention may include, for example, a step of producing 3-hydroxytetrahydrofuran as the raw material in step B, before hydrogenation reaction step B. The step of producing 3-hydroxytetrahydrofuran particularly includes hydrogenation reaction step A (or dehydration reaction step and hydrogenation reaction step A) in the method for producing 3-hydroxytetrahydrofuran of the present invention.

EXAMPLES

Hereinafter, the present invention is more specifically described with reference to Examples, but the present invention is not limited to these Examples.

Example 1a

Production of Catalyst (9.9% by Weight $WO_X/C$)

Ammonium tungstate (manufactured by Wako Pure Chemical Industries, Ltd.) (0.1402 g) was dissolved in 15 mL of distilled water at 70 to 90° C., to prepare an aqueous solution. Then, the total amount of the aqueous solution was added to 0.9013 g of carbon black (product name "Vulcan XC72", manufactured by Cabot Corporation) in five portions so that no liquid pool was made, and the resultant was heated and stirred at 70 to 90° C. for impregnation. After such impregnation, the resultant was dried in a dryer at 110° C. overnight.

Then, the total amount of the resultant was packed in a flow-through type catalytic reduction apparatus having an inner diameter of 0.6 cm, and the temperature was raised at a rate of 10° C./min., while hydrogen was allowed to flow through at 30 cc/min. After the temperature reached 500° C., that temperature was maintained for 30 minutes to perform a reduction treatment.

Thereafter, the resultant was cooled to room temperature over 30 minutes, hydrogen was then switched to a 2% oxygen (balance: He) gas, and passivation was performed for 2 hours to provide a catalyst (9.9% by weight $WO_X$/C).

Example 2a

Production of Catalyst (9.9% by Weight $WO_X$—Pd/C)

Ammonium tungstate (manufactured by Wako Pure Chemical Industries, Ltd.) (0.1402 g) was dissolved in 15 mL of distilled water at 70 to 90° C., to prepare an aqueous solution. In addition, an aqueous solution in which 0.2818 g of an aqueous palladium (II) nitrate solution (Pd: 5.07%, manufactured by N. E. Chemcat Corporation) was diluted with 5 mL of distilled water was prepared. Then, the total amount of the aqueous ammonium tungstate solution was added to 0.8870 g of carbon black (product name "Vulcan XC72", manufactured by Cabot Corporation) in five portions so that no liquid pool was made, and the resultant was heated and stirred at 70 to 90° C. for impregnation. After this resultant was dried in a dryer at 110° C. overnight, the total amount of the dilute aqueous palladium (II) nitrate solution was added thereto in two portions so that no liquid pool was made, and the resultant was heated and stirred at 70 to 90° C. for impregnation. After such impregnation, the resultant was dried in a dryer at 110° C. overnight to provide a catalyst (9.9% by weight $WO_X$—Pd/C).

Example 3a

Production of Catalyst (9.9% by Weight $WO_X$—Pt/C)

Ammonium tungstate (manufactured by Wako Pure Chemical Industries, Ltd.) (0.1402 g) was dissolved in 15 mL of distilled water at 70 to 90° C., to prepare an aqueous solution. In addition, a solution in which 0.0528 g of bis(acetylacetonato)platinum was dissolved in 5 mL of acetone was prepared. Then, the total amount of the aqueous ammonium tungstate solution was added to 0.8751 g of carbon black (product name "Vulcan XC72", manufactured by Cabot Corporation) in five portions so that no liquid pool was made, and the resultant was heated and stirred at 70 to 90° C. for impregnation. After this resultant was dried in a dryer at 110° C. overnight, the total amount of the solution of bis(acetylacetonato)platinum was added thereto in two portions so that no liquid pool was made, and the resultant was heated and stirred at 70 to 90° C. for impregnation. After such impregnation, the resultant was dried in a dryer at 110° C. overnight to provide a catalyst (9.9% by weight $WO_X$—Pt/C).

Example 4a

Production of Catalyst (9.9% by Weight $WO_X$—Fe/C)

Ammonium tungstate (manufactured by Wako Pure Chemical Industries, Ltd.) (0.1402 g) was dissolved in 15 mL of distilled water at 70 to 90° C., to prepare an aqueous solution. In addition, an aqueous solution in which 0.0542 g of iron (III) nitrate nonahydrate was dissolved in 5 mL of water was prepared. Then, the total amount of the aqueous ammonium tungstate solution was added to 0.8938 g of carbon black (product name "Vulcan XC72", manufactured by Cabot Corporation) in five portions so that no liquid pool was made, and the resultant was heated and stirred at 70 to 90° C. for impregnation. After this resultant was dried in a dryer at 110° C. overnight, the total amount of the aqueous iron (III) nitrate solution was added thereto in two portions so that no liquid pool was made, and the resultant was heated and stirred at 70 to 90° C. for impregnation. After such impregnation, the resultant was dried in a dryer at 110° C. overnight.

Then, the total amount of the resultant was packed in a flow-through type catalytic reduction apparatus having an inner diameter of 0.6 cm, and the temperature was raised at a rate of 10° C./min., while hydrogen was allowed to flow through at 30 cc/min. After the temperature reached 500° C., that temperature was maintained for 30 minutes to perform a reduction treatment.

Thereafter, the resultant was cooled to room temperature over 30 minutes, hydrogen was then switched to a 2% oxygen (balance: He) gas, and passivation was performed for 2 hours to provide a catalyst (9.9% by weight $WO_X$—Fe/C).

Example 5a

Production of Catalyst (9.9% by Weight $WO_X$—Co/C)

Ammonium tungstate (manufactured by Wako Pure Chemical Industries, Ltd.) (0.1402 g) was dissolved in 15 mL of distilled water at 70 to 90° C., to prepare an aqueous solution. In addition, an aqueous solution in which 0.0391 g of cobalt (II) nitrate hexahydrate was dissolved in 5 mL of water was prepared. Then, the total amount of the aqueous ammonium tungstate solution was added to 0.8938 g of carbon black (product name "Vulcan XC72", manufactured by Cabot Corporation) in five portions so that no liquid pool was made, and the resultant was heated and stirred at 70 to 90° C. for impregnation. After this resultant was dried in a dryer at 110° C. overnight, the total amount of the aqueous cobalt (II) nitrate solution was added thereto in two portions so that no liquid pool was made, and the resultant was heated and stirred at 70 to 90° C. for impregnation. After such impregnation, the resultant was dried in a dryer at 110° C. overnight.

Then, the total amount of the resultant was packed in a flow-through type catalytic reduction apparatus having an inner diameter of 0.6 cm, and the temperature was raised at a rate of 10° C./min., while hydrogen was allowed to flow through at 30 cc/min. After the temperature reached 500° C., that temperature was maintained for 30 minutes to perform a reduction treatment.

Thereafter, the resultant was cooled to room temperature over 30 minutes, hydrogen was then switched to a 2% oxygen (balance: He) gas, and passivation was performed for 2 hours to provide a catalyst (9.9% by weight $WO_X$—Co/C).

Example 6a

Production of Catalyst (9.9% by Weight $WO_X$—Ni/C)

Ammonium tungstate (manufactured by Wako Pure Chemical Industries, Ltd.) (0.1402 g) was dissolved in 15 mL of distilled water at 70 to 90° C., to prepare an aqueous solution. In addition, an aqueous solution in which 0.0391 g of nickel (II) nitrate hexahydrate was dissolved in 5 mL of water was prepared. Then, the total amount of the aqueous ammonium tungstate solution was added to 0.8934 g of carbon black (product name "Vulcan XC72", manufactured by Cabot Corporation) in five portions so that no liquid pool was made, and the resultant was heated and stirred at 70 to 90° C. for impregnation. After this resultant was dried in a dryer at 110° C. overnight, the total amount of the aqueous nickel (II) nitrate solution was added thereto in two portions so that no liquid pool was made, and the resultant was heated and stirred at 70 to 90° C. for impregnation. After such impregnation, the resultant was dried in a dryer at 110° C. overnight.

Then, the total amount of the resultant was packed in a flow-through type catalytic reduction apparatus having an inner diameter of 0.6 cm, and the temperature was raised at a rate of 10° C./min., while hydrogen was allowed to flow through at 30 cc/min. After the temperature reached 500° C., that temperature was maintained for 30 minutes to perform a reduction treatment.

Thereafter, the resultant was cooled to room temperature over 30 minutes, hydrogen was then switched to a 2% oxygen (balance: He) gas, and passivation was performed for 2 hours to provide a catalyst (9.9% by weight $WO_X$—Ni/C).

Example 7a

Production of Catalyst (9.9% by Weight $WO_X$—Cu/C)

Ammonium tungstate (manufactured by Wako Pure Chemical Industries, Ltd.) (0.1402 g) was dissolved in 15 mL of distilled water at 70 to 90° C., to prepare an aqueous solution. In addition, an aqueous solution in which 0.0324 g of copper (II) nitrate trihydrate was dissolved in 5 mL of water was prepared. Then, the total amount of the aqueous ammonium tungstate solution was added to 0.8927 g of carbon black (product name "Vulcan XC72", manufactured by Cabot Corporation) in five portions so that no liquid pool was made, and the resultant was heated and stirred at 70 to 90° C. for impregnation. After this resultant was dried in a dryer at 110° C. overnight, the total amount of the copper (II) nitrate solution was added thereto in two portions so that no liquid pool was made, and the resultant was heated and stirred at 70 to 90° C. for impregnation. After such impregnation, the resultant was dried in a dryer at 110° C. overnight.

Then, the total amount of the resultant was packed in a flow-through type catalytic reduction apparatus having an inner diameter of 0.6 cm, and the temperature was raised at a rate of 10° C./min., while hydrogen was allowed to flow through at 30 cc/min. After the temperature reached 500° C., that temperature was maintained for 30 minutes to perform a reduction treatment.

Thereafter, the resultant was cooled to room temperature over 30 minutes, hydrogen was then switched to a 2% oxygen (balance: He) gas, and passivation was performed for 2 hours to provide a catalyst (9.9% by weight $WO_X$—Cu/C).

Example 1-1

Production of 3-hydroxytetrahydrofuran

An inner glass cylinder for an autoclave was charged with a stirrer chip, 150 mg of the catalyst (9.9% by weight $WO_X$/C) weighed which is obtained in Example 1a, 4 g of 1,4-dioxane and 1 g of 1,4-anhydroerythritol. The inner cylinder for an autoclave was placed in a 190-mL autoclave, and the lid of the autoclave was closed. Then, an operation of feeding 1 MPa of hydrogen into the autoclave and thereafter evacuating the atmosphere in the autoclave was repeated three times, to expel the air in the autoclave from the autoclave. The autoclave was filled with hydrogen so that a pressure of 8 MPa was shown at the reaction temperature of 180° C. and a pressure of 5 MPa was shown at room temperature.

Subsequently, the autoclave was set to a heating apparatus equipped with a magnetic stirrer, and heated for 16 hours so that the temperature in the reactor (in the autoclave) was 180° C. Thereafter, the temperature was decreased to room temperature, and hydrogen in the autoclave was released for pressure release.

The solution after the reaction was analyzed using gas chromatography (gas chromatographic apparatus: "GC-2014" (manufactured by Shimadzu Corporation), GC column: TC-WAX, DB-FFAP, detector: FID). Thus, the conversion of 1,4-anhydroerythritol and the selectivity of the product were calculated. The analysis results are shown in Table 2.

Examples 1-2 to 1-7

Production of 3-hydroxytetrahydrofuran was performed in the same manner as in Example 1-1 except that the catalyst used was changed to each catalyst shown in Table 1. The results are shown in Table 2. Herein, the temperature recited in the column "Reduction treatment" in Table 1 indicates the temperature of the reduction treatment in catalyst production. "None" in the column "Reduction treatment" in Table 1 means that no reduction treatment was performed in catalyst production, and the same shall apply also in Examples below. In addition, "M/W" in Table 1 means the proportion (molar ratio) of a metal other than tungsten to tungsten (W) supported on the carrier.

TABLE 1

| Catalyst | | M/W Molar ratio | Amount of catalyst (mg) | Reduction treatment (K) | Reaction temperature (K) | Hydrogen pressure (MPa) | Reaction time (h) |
|---|---|---|---|---|---|---|---|
| Structure | Production | | | | | | |
| Example 1-1 | 9.9% by weight $WO_X$/C | Example 1a | 0 | 150 | 773 | 453 | 8.0 | 16 |
| Example 1-2 | 9.9% by weight $WO_X$—Pd/C | Example 2a | 0.25 | 150 | None | 453 | 8.0 | 16 |
| Example 1-3 | 9.9% by weight $WO_X$—Pt/C | Example 3a | 0.25 | 150 | None | 453 | 8.0 | 16 |

TABLE 1-continued

|  | Catalyst | | M/W Molar ratio | Amount of catalyst (mg) | Reduction treatment (K) | Reaction temperature (K) | Hydrogen pressure (MPa) | Reaction time (h) |
| --- | --- | --- | --- | --- | --- | --- | --- | --- |
|  | Structure | Production | | | | | | |
| Example 1-4 | 9.9% by weight $WO_x$—Fe/C | Example 4a | 0.25 | 150 | 773 | 453 | 8.0 | 16 |
| Example 1-5 | 9.9% by weight $WO_x$—Co/C | Example 5a | 0.25 | 150 | 773 | 453 | 8.0 | 16 |
| Example 1-6 | 9.9% by weight $WO_x$—Ni/C | Example 6a | 0.25 | 150 | 773 | 453 | 8.0 | 16 |
| Example 1-7 | 9.9% by weight $WO_x$—Cu/C | Example 7a | 0.25 | 150 | 773 | 453 | 8.0 | 16 |

TABLE 2

|  | Conversion (%) | Selectivity (%) | | | | | | | | | | |
| --- | --- | --- | --- | --- | --- | --- | --- | --- | --- | --- | --- | --- |
|  |  | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 1-1 | 16.5 | 16.0 | 47.8 | 5.7 | 0.0 | 0.0 | 2.9 | 0.0 | 6.0 | 0.0 | 2.5 | 19.1 |
| Example 1-2 | 43.7 | 8.3 | 68.9 | 1.2 | 0.0 | 0.0 | 9.5 | 0.0 | 0.7 | 0.0 | 1.1 | 10.2 |
| Example 1-3 | 47.5 | 3.5 | 63.4 | 1.8 | 0.0 | 0.0 | 11.2 | 0.0 | 1.8 | 0.4 | 1.2 | 16.8 |
| Example 1-4 | 11.8 | 2.4 | 50.7 | 1.9 | 0.0 | 0.0 | 3.6 | 0.0 | 1.2 | 0.0 | 1.6 | 38.6 |
| Example 1-5 | 17.8 | 3.0 | 56.3 | 4.4 | 0.0 | 0.0 | 2.7 | 0.0 | 1.0 | 0.0 | 2.1 | 30.5 |
| Example 1-6 | 24.2 | 7.5 | 53.3 | 4.9 | 0.0 | 0.0 | 3.5 | 0.0 | 1.3 | 0.0 | 1.9 | 27.6 |
| Example 1-7 | 17.2 | 5.0 | 61.2 | 0.0 | 0.0 | 0.0 | 4.4 | 0.0 | 2.4 | 0.0 | 2.7 | 24.4 |

Example 8a

Production of Catalyst (9.9% by Weight $WO_x$/C BP2000)

A catalyst (9.9% by weight $WO_x$/C) was obtained in the same manner as in Example 1a except that 0.9013 g of "BP2000" (product name) (carbon black, manufactured by Cabot Corporation) was used instead of "Vulcan XC72" (product name) (carbon black, manufactured by Cabot Corporation).

Example 9a

Production of Catalyst (9.9% by Weight $WO_x$/C Shirasagi FAC-10)

A catalyst (9.9% by weight $WO_x$/C) was obtained in the same manner as in Example 1a except that 0.9013 g of "Shirasagi FAC-10" (product name) (carbon black, manufactured by Japan EnviroChemicals, Ltd.) was used instead of "Vulcan XC72" (product name) (carbon black, manufactured by Cabot Corporation).

Example 10a

Production of Catalyst (9.9% by Weight $WO_x$/C Shirasagi M)

A catalyst (9.9% by weight $WO_x$/C) was obtained in the same manner as in Example 1a except that 0.9013 g of "Shirasagi M" (product name) (carbon black, manufactured by Japan EnviroChemicals, Ltd.) was used instead of "Vulcan XC72" (product name) (carbon black, manufactured by Cabot Corporation).

Example 11a

Production of Catalyst (9.9% by Weight $WO_x$/C Shirasagi C)

A catalyst (9.9% by weight $WO_x$/C) was obtained in the same manner as in Example 1a except that 0.9013 g of "Shirasagi C" (product name) (carbon black, manufactured by Japan EnviroChemicals, Ltd.) was used instead of "Vulcan XC72" (product name) (carbon black, manufactured by Cabot Corporation).

Example 12a

Production of Catalyst (9.9% by Weight $WO_x$/C Carboraffin)

A catalyst (9.9% by weight $WO_x$/C) was obtained in the same manner as in Example 1a except that 0.9013 g of "Carboraffin" (product name) (carbon black, manufactured by Japan EnviroChemicals, Ltd.) was used instead of "Vulcan XC72" (product name) (carbon black, manufactured by Cabot Corporation).

Example 13a

Production of Catalyst (9.9% by weight $WO_x/TiO_2$)

A catalyst (9.9% by weight $WO_x/TiO_2$) was obtained in the same manner as in Example 1a except that 0.9013 g of "TIO-4" (product name) (titania, manufactured by Nippon Aerosil Co., Ltd.) was used instead of "Vulcan XC72" (product name) (carbon black, manufactured by Cabot Corporation).

Example 14a

Production of Catalyst (9.9% by Weight $WO_x/ZrO_2$)

A catalyst (9.9% by weight $WO_x/ZrO_2$) was obtained in the same manner as in Example 1a except that 0.9013 g of zirconia (manufactured by Wako Pure Chemical Industries, Ltd.) was used instead of "Vulcan XC72" (product name) (carbon black, manufactured by Cabot Corporation).

Example 15a

Production of Catalyst (9.9% by Weight $WO_x/MgO$)

A catalyst (9.9% by weight $WO_x/MgO$) was obtained in the same manner as in Example 1a except that 0.9013 g of "500A" (product name) (magnesia, manufactured by Ube Industries, Ltd.) was used instead of "Vulcan XC72" (product name) (carbon black, manufactured by Cabot Corporation).

Example 16a

Production of Catalyst (9.9% by weight $WO_x/SiO_2$)

A catalyst (9.9% by weight $WO_x/SiO_2$) was obtained in the same manner as in Example 1a except that 0.9013 g of "G-6" (product name) (silica, manufactured by Fuji Silysia Chemical Ltd.) was used instead of "Vulcan XC72" (product name) (carbon black, manufactured by Cabot Corporation).

Example 17a

Production of Catalyst (9.9% by Weight $WO_x/Al_2O_3$)

A catalyst (9.9% by weight $WO_x/Al_2O_3$) was obtained in the same manner as in Example 1a except that 0.9013 g of "KHO-24" (product name) (alumina, manufactured by Sumitomo Chemical Co., Ltd.) was used instead of "Vulcan XC72" (product name) (carbon black, manufactured by Cabot Corporation).

Examples 2-1 to 2-11

Production of 3-hydroxytetrahydrofuran was performed in the same manner as in Example 1-1 except that the catalyst used was changed to each catalyst shown in Table 3. The results are shown in Table 4.

TABLE 3

| | Catalyst | | Amount of catalyst (mg) | Reduction treatment (K) | Reaction temperature (K) | Hydrogen pressure (MPa) | Reaction time (h) |
|---|---|---|---|---|---|---|---|
| | Structure | Production | | | | | |
| Example 2-1 | 9.9% by weight $WO_x/C$ | Example 1a | 150 | 773 | 453 | 8.0 | 16 |
| Example 2-2 | 9.9% by weight $WO_x/C$ | Example 8a | 150 | 773 | 453 | 8.0 | 16 |
| Example 2-3 | 9.9% by weight $WO_x/C$ | Example 9a | 150 | 773 | 453 | 8.0 | 16 |
| Example 2-4 | 9.9% by weight $WO_x/C$ | Example 10a | 150 | 773 | 453 | 8.0 | 16 |
| Example 2-5 | 9.9% by weight $WO_x/C$ | Example 11a | 150 | 773 | 453 | 8.0 | 16 |
| Example 2-6 | 9.9% by weight $WO_x/C$ | Example 12a | 150 | 773 | 453 | 8.0 | 16 |
| Example 2-7 | 9.9% by weight $WO_x/TiO_2$ | Example 13a | 150 | 773 | 453 | 8.0 | 16 |
| Example 2-8 | 9.9% by weight $WO_x/ZrO_2$ | Example 14a | 150 | 773 | 453 | 8.0 | 16 |
| Example 2-9 | 9.9% by weight $WO_x/MgO$ | Example 15a | 150 | 773 | 453 | 8.0 | 16 |
| Example 2-10 | 9.9% by weight $WO_x/SiO_2$ | Example 16a | 150 | 773 | 453 | 8.0 | 16 |
| Example 2-11 | 9.9% by weight $WO_x/Al_2O_3$ | Example 17a | 150 | 773 | 453 | 8.0 | 16 |

TABLE 4

| | Conversion (%) | Selectivity (%) | | | | | | | | | | |
|---|---|---|---|---|---|---|---|---|---|---|---|---|
| | | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 2-1 | 16.5 | 16.0 | 47.8 | 5.7 | 0.0 | 0.0 | 2.9 | 0.0 | 6.0 | 0.0 | 2.5 | 19.1 |
| Example 2-2 | 13.1 | 3.4 | 61.0 | 0.0 | 0.0 | 0.0 | 0.0 | 0.0 | 0.0 | 0.0 | 2.7 | 32.9 |

TABLE 4-continued

| | Conversion (%) | Selectivity (%) | | | | | | | | | | |
|---|---|---|---|---|---|---|---|---|---|---|---|---|
| | | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 2-3 | 13.3 | 7.0 | 49.4 | 4.1 | 0.0 | 0.0 | 0.0 | 0.0 | 2.0 | 0.0 | 3.4 | 34.0 |
| Example 2-4 | 13.3 | 2.4 | 57.9 | 3.0 | 0.0 | 0.0 | 1.1 | 0.0 | 1.2 | 0.0 | 3.1 | 31.2 |
| Example 2-5 | 9.5 | 6.3 | 19.1 | 13.9 | 0.0 | 0.0 | 0.0 | 0.0 | 2.7 | 0.0 | 0.0 | 58.1 |
| Example 2-6 | 6.1 | 6.2 | 35.8 | 3.7 | 0.0 | 0.0 | 0.0 | 0.0 | 2.3 | 0.0 | 2.7 | 49.1 |
| Example 2-7 | 14.5 | 1.2 | 65.5 | 2.1 | 0.0 | 0.0 | 3.8 | 0.0 | 1.1 | 0.0 | 2.3 | 24.0 |
| Example 2-8 | 12.6 | 4.9 | 48.1 | 3.2 | 0.0 | 0.0 | 4.8 | 0.0 | 2.1 | 0.0 | 2.0 | 34.9 |
| Example 2-9 | 1.7 | 15.4 | 19.8 | 0.0 | 0.0 | 0.0 | 0.0 | 0.0 | 8.8 | 0.0 | 11.6 | 44.5 |
| Example 2-10 | 15.2 | 5.2 | 60.2 | 3.6 | 0.0 | 0.0 | 1.7 | 0.0 | 1.2 | 0.0 | 3.9 | 24.2 |
| Example 2-11 | 11.2 | 1.5 | 69.6 | 0.0 | 0.0 | 0.0 | 0.0 | 0.0 | 0.0 | 0.0 | 0.0 | 28.9 |

Example 18a

Production of Catalyst (9.9% by weight $WO_X$—Pd/C)

A catalyst (9.9% by weight $WO_X$—Pd/C; W/Pd=0.25) was obtained in the same manner as in Example 2a except that the amount of the aqueous palladium (II) nitrate solution (Pd: 5.07%, manufactured by N. E. Chemcat Corporation) used was changed to 4.0588 g.

Example 19a

Production of Catalyst (9.9% by Weight $WO_X$—Pd/$TiO_2$)

Ammonium tungstate (manufactured by Wako Pure Chemical Industries, Ltd.) (0.1402 g) was dissolved in 15 mL of distilled water at 70 to 90° C., to prepare an aqueous solution. In addition, an aqueous solution in which 4.0588 g of an aqueous palladium (II) nitrate solution (Pd: 5.07%, manufactured by N. E. Chemcat Corporation) was diluted with 5 mL of distilled water was prepared. Then, the total amount of the aqueous ammonium tungstate solution was added to 0.9013 g of "TIO-4" (product name) (titania, manufactured by Nippon Aerosil Co., Ltd.) in five portions so that no liquid pool was made, and the resultant was heated and stirred at 70 to 90° C. for impregnation. After this resultant was dried in a dryer at 110° C. overnight, the total amount of the dilute aqueous palladium (II) nitrate solution was added thereto in two portions so that no liquid pool was made, and the resultant was heated and stirred at 70 to 90° C. for impregnation. After such impregnation, the resultant was dried in a dryer at 110° C. overnight to provide a catalyst (9.9% by weight $WO_X$—Pd/$TiO_2$; W/Pd=0.25).

Example 20a

Production of Catalyst (9.9% by Weight $WO_X$—Pd/$Al_2O_3$)

A catalyst (9.9% by weight $WO_X$—Pd/$Al_2O_3$; W/Pd=0.25) was obtained in the same manner as in Example 19a except that 0.9013 g of "KHO-24" (product name) (alumina, manufactured by Sumitomo Chemical Co., Ltd.) was used instead of "TIO-4" (product name) (titania, manufactured by Nippon Aerosil Co., Ltd.).

Example 21a

Production of Catalyst (9.9% by weight $WO_X$—Pd/C)

Ammonium tungstate (manufactured by Wako Pure Chemical Industries, Ltd.) (0.1402 g) was dissolved in 15 mL of distilled water at 70 to 90° C., to prepare an aqueous solution. In addition, an aqueous solution in which 4.0588 g of an aqueous palladium (II) nitrate solution (Pd: 5.07%, manufactured by N. E. Chemcat Corporation) was dissolved in 5 mL of distilled water was prepared. Then, the total amount of the aqueous ammonium tungstate solution was added to 0.8870 g of carbon black (product name "Vulcan XC72", manufactured by Cabot Corporation) in five portions so that no liquid pool was made, and the resultant was heated and stirred at 70 to 90° C. for impregnation. After this resultant was dried in a dryer at 110° C. overnight, the total amount of the dilute aqueous palladium (II) nitrate solution was added thereto in two portions so that no liquid pool was made, and the resultant was heated and stirred at 70 to 90° C. for impregnation. After such impregnation, the resultant was dried in a dryer at 110° C. overnight.

Then, the total amount of the resultant was packed in a flow-through type catalytic reduction apparatus having an inner diameter of 0.6 cm, and the temperature was raised at a rate of 10° C./min., while hydrogen was allowed to flow through at 30 cc/min. After the temperature reached 500° C., that temperature was maintained for 30 minutes to perform a reduction treatment.

Thereafter, the resultant was cooled to room temperature over 30 minutes, hydrogen was then switched to a 2% oxygen (balance: He) gas, and passivation was performed for 2 hours to provide a catalyst (9.9% by weight $WO_X$—Pd/C; W/Pd=0.25).

Example 22a

Production of Catalyst (9.9% by Weight $WO_X$—Pd/$TiO_2$)

Ammonium tungstate (manufactured by Wako Pure Chemical Industries, Ltd.) (0.1402 g) was dissolved in 15 mL of distilled water at 70 to 90° C., to prepare an aqueous solution. In addition, an aqueous solution in which 4.0588 g of an aqueous palladium (II) nitrate solution (Pd: 5.07%, manufactured by N. E. Chemcat Corporation) was diluted with 5 mL of distilled water was prepared. Then, the total amount of the aqueous ammonium tungstate solution was added to 0.9013 g of "TIO-4" (product name) (titania, manufactured by Nippon Aerosil Co., Ltd.) in five portions so that no liquid pool was made, and the resultant was heated and stirred at 70 to 90° C. for impregnation. After this resultant was dried in a dryer at 110° C. overnight, the total amount of the dilute aqueous palladium (II) nitrate solution was added thereto in two portions so that no liquid pool was made, and the resultant was heated and stirred at 70 to 90° C. for impregnation. After such impregnation, the resultant was dried in a dryer at 110° C. overnight.

Then, the total amount of the resultant was packed in a flow-through type catalytic reduction apparatus having an inner diameter of 0.6 cm, and the temperature was raised at a rate of 10° C./min., while hydrogen was allowed to flow through at 30 cc/min. After the temperature reached 500° C., that temperature was maintained for 30 minutes to perform a reduction treatment.

Thereafter, the resultant was cooled to room temperature over 30 minutes, hydrogen was then switched to a 2% oxygen (balance: He) gas, and passivation was performed for 2 hours to provide a catalyst (9.9% by weight $WO_X$—Pd/$TiO_2$; W/Pd=0.25).

Example 23a

Production of Catalyst (9.9% by Weight $WO_X$—Pd/$Al_2O_3$)

A catalyst (9.9% by weight $WO_X$—Pd/$Al_2O_3$; W/Pd=0.25) was obtained in the same manner as in Example 22a except that 0.9013 g of "KHO-24" (product name) (alumina, manufactured by Sumitomo Chemical Co., Ltd.) was used instead of "TIO-4" (product name) (titania, manufactured by Nippon Aerosil Co., Ltd.).

Examples 3-1 to 3-6

Production of 3-hydroxytetrahydrofuran was performed in the same manner as in Example 1-1 except that the catalyst used was changed to each catalyst shown in Table 5. The results are shown in Table 6. Herein, "W/Pd" in Table 5 means the proportion (molar ratio) of tungsten (W) to palladium (Pd) supported on the carrier.

TABLE 5

| | Catalyst | | W/Pd Molar ratio | Amount of catalyst (mg) | Reduction treatment (K) | Reaction temperature (K) | Hydrogen pressure (MPa) | Reaction time (h) |
|---|---|---|---|---|---|---|---|---|
| | Structure | Production | | | | | | |
| Example 3-1 | 9.9% by weight $WO_X$—Pd/C | Example 18a | 0.25 | 150 | None | 453 | 8.0 | 16 |
| Example 3-2 | 9.9% by weight $WO_X$—Pd/$TiO_2$ | Example 19a | 0.25 | 150 | None | 453 | 8.0 | 16 |
| Example 3-3 | 9.9% by weight $WO_X$—Pd/$Al_2O_3$ | Example 20a | 0.25 | 150 | None | 453 | 8.0 | 16 |
| Example 3-4 | 9.9% by weight $WO_X$—Pd/C | Example 21a | 0.25 | 150 | 773 | 453 | 8.0 | 16 |
| Example 3-5 | 9.9% by weight $WO_X$—Pd/$TiO_2$ | Example 22a | 0.25 | 150 | 773 | 453 | 8.0 | 16 |
| Example 3-6 | 9.9% by weight $WO_X$—Pd/$Al_2O_3$ | Example 23a | 0.25 | 150 | 773 | 453 | 8.0 | 16 |

TABLE 6

| | Conversion (%) | Selectivity (%) | | | | | | | | | | |
|---|---|---|---|---|---|---|---|---|---|---|---|---|
| | | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 3-1 | 44.3 | 7.7 | 69.1 | 0.7 | 0.0 | 0.0 | 6.6 | 0.0 | 0.5 | 0.0 | 1.4 | 14.0 |
| Example 3-2 | 29.9 | 18.7 | 51.2 | 0.0 | 1.0 | 0.0 | 0.0 | 0.0 | 1.0 | 0.0 | 3.1 | 25.0 |
| Example 3-3 | 22.0 | 7.8 | 64.5 | 1.5 | 0.0 | 0.0 | 3.3 | 0.0 | 1.1 | 0.0 | 8.0 | 13.8 |
| Example 3-4 | 53.6 | 2.4 | 65.8 | 1.5 | 0.0 | 0.0 | 10.5 | 0.0 | 1.3 | 0.4 | 1.3 | 16.7 |
| Example 3-5 | 30.4 | 13.7 | 56.0 | 0.0 | 0.0 | 0.0 | 4.4 | 0.0 | 1.6 | 0.0 | 5.5 | 18.7 |
| Example 3-6 | 25.4 | 2.9 | 69.8 | 0.0 | 0.0 | 0.0 | 8.1 | 0.0 | 0.6 | 0.0 | 2.1 | 16.5 |

Example 24a

Production of Catalyst (3.3% by Weight $WO_x$—Pd/C)

A catalyst (3.3% by weight $WO_x$—Pd/C) was obtained in the same manner as in Example 2a except that the amount of ammonium tungstate used was changed to 0.0467 g and the amount of the aqueous palladium (II) nitrate solution used was changed to 0.0939 g.

Example 25a

Production of Catalyst (6.6% by Weight $WO_x$—Pd/C)

A catalyst (6.6% by weight $WO_x$—Pd/C) was obtained in the same manner as in Example 2a except that the amount of ammonium tungstate used was changed to 0.0935 g and the amount of the aqueous palladium (II) nitrate solution used was changed to 0.1879 g.

Example 26a

Production of Catalyst (13.2% by Weight $WO_x$—Pd/C)

A catalyst (13.2% by weight $WO_x$—Pd/C) was obtained in the same manner as in Example 2a except that the amount of ammonium tungstate used was changed to 0.1869 g and the amount of the aqueous palladium (II) nitrate solution used was changed to 2.1879 g.

Examples 4-1 to 4-4

Production of 3-hydroxytetrahydrofuran was performed in the same manner as in Example 1-1 except that the catalyst used was changed to each catalyst shown in Table 7. The results are shown in Table 8. Herein, "Pd/W" in Table 7 means the proportion (molar ratio) of palladium (Pd) to tungsten (W) supported on the carrier, and the same shall also apply below.

TABLE 7

| | Catalyst | | Pd/W Molar ratio | Amount of catalyst (mg) | Reduction treatment (K) | Reaction temperature (K) | Hydrogen pressure (MPa) | Reaction time (h) |
|---|---|---|---|---|---|---|---|---|
| | Structure | Production | | | | | | |
| Example 4-1 | 3.3% by weight $WO_x$—Pd/C | Example 24a | 0.25 | 150 | None | 453 | 8.0 | 16 |
| Example 4-2 | 6.6% by weight $WO_x$—Pd/C | Example 25a | 0.25 | 150 | None | 453 | 8.0 | 16 |
| Example 4-3 | 9.9% by weight $WO_x$—Pd/C | Example 2a | 0.25 | 150 | None | 453 | 8.0 | 16 |
| Example 4-4 | 13.2% by weight $WO_x$—Pd/C | Example 26a | 0.25 | 150 | None | 453 | 8.0 | 16 |

TABLE 8

| | Conversion (%) | Selectivity (%) | | | | | | | | | |
|---|---|---|---|---|---|---|---|---|---|---|---|
| | | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 4-1 | 23.0 | 4.6 | 70.2 | 0.0 | 0.0 | 0.0 | 1.8 | 0.0 | 0.0 | 0.0 | 1.3 | 22.1 |
| Example 4-2 | 32.6 | 4.9 | 72.0 | 0.0 | 0.0 | 0.0 | 4.9 | 0.0 | 0.0 | 0.0 | 1.3 | 16.9 |
| Example 4-3 | 44.3 | 7.7 | 69.1 | 0.7 | 0.0 | 0.0 | 6.6 | 0.0 | 0.5 | 0.0 | 1.4 | 14.0 |
| Example 4-4 | 45.4 | 6.3 | 66.4 | 0.8 | 0.0 | 0.0 | 7.2 | 0.0 | 0.4 | 0.0 | 0.8 | 18.1 |

Example 27a

Production of Catalyst (9.9% by Weight $WO_X$—Pd/C; Pd/W=0.032)

A catalyst (9.9% by weight $WO_X$—Pd/C; Pd/W=0.032) was obtained in the same manner as in Example 2a except that the amount of the aqueous palladium (II) nitrate solution used was changed to 0.0352 g.

Example 28a

Production of Catalyst (9.9% by Weight $WO_X$—Pd/C, Pd/W=0.063)

A catalyst (9.9% by weight $WO_X$—Pd/C, Pd/W=0.063) was obtained in the same manner as in Example 2a except that the amount of the aqueous palladium (II) nitrate solution used was changed to 0.0705 g.

Example 29a

Production of Catalyst (9.9% by Weight $WO_X$—Pd/C, Pd/W=0.13)

A catalyst (9.9% by weight $WO_X$—Pd/C, Pd/W=0.13) was obtained in the same manner as in Example 2a except that the amount of the aqueous palladium (II) nitrate solution used was changed to 0.1409 g.

Example 30a

Production of Catalyst (9.9% by Weight $WO_X$—Pd/C, Pd/W=0.5)

A catalyst (9.9% by weight $WO_X$—Pd/C, Pd/W=0.5) was obtained in the same manner as in Example 2a except that the amount of the aqueous palladium (II) nitrate solution used was changed to 0.5636 g.

Example 31a

Production of Catalyst (9.9% by Weight $WO_X$—Pd/C, Pd/W=1)

A catalyst (9.9% by weight $WO_X$—Pd/C, Pd/W=1) was obtained in the same manner as in Example 2a except that the amount of the aqueous palladium (II) nitrate solution used was changed to 1.1272 g.

Example 32a

Production of Catalyst (9.9% by Weight $WO_X$—Pd/C, Pd/W=2)

A catalyst (9.9% by weight $WO_X$—Pd/C, Pd/W=2) was obtained in the same manner as in Example 2a except that the amount of the aqueous palladium (II) nitrate solution used was changed to 2.2544 g.

Example 33a

Production of Catalyst (1.4% by Weight Pd/C)

An aqueous palladium (II) nitrate solution (Pd: 5.07%) (0.2818 g) was diluted with 5 mL of distilled water to prepare an aqueous solution. Then, the total amount of the aqueous solution was added to 0.9857 g of carbon black (product name "Vulcan XC72", manufactured by Cabot Corporation) in three portions so that no liquid pool was made, and the resultant was heated and stirred at 70 to 90° C. for impregnation. After such impregnation, the resultant was dried in a dryer at 110° C. overnight to provide a catalyst (1.4% by weight Pd/C).

Examples 5-1 to 5-9

Production of 3-hydroxytetrahydrofuran was performed in the same manner as in Example 1-1 except that the catalyst used was changed to each catalyst shown in Table 9. The results are shown in Table 10. Herein, "(0.25)" in the column "Molar ratio Pd/W" of Examples 5-9 in Table 9 means the amount of Pd supported on the carrier in the catalyst used (1.4% by weight Pd/C) was the same as the amount of Pd supported on the carrier in the catalyst used (9.9% by weight $WO_X$—Pd/C obtained in Example 2a) in Example 5-5.

TABLE 9

| | Catalyst | | Pd/W Molar ratio | Amount of catalyst (mg) | Reduction treatment (K) | Reaction temperature (K) | Hydrogen pressure (MPa) | Reaction time (h) |
|---|---|---|---|---|---|---|---|---|
| | Structure | Production | | | | | | |
| Example 5-1 | 9.9% by weight $WO_X$/C | Example 1a | 0 | 150 | 773 | 453 | 8.0 | 16 |
| Example 5-2 | 9.9% by weight $WO_X$—Pd/C | Example 27a | 0.032 | 150 | None | 453 | 8.0 | 16 |
| Example 5-3 | 9.9% by weight $WO_X$—Pd/C | Example 28a | 0.063 | 150 | None | 453 | 8.0 | 16 |
| Example 5-4 | 9.9% by weight $WO_X$—Pd/C | Example 29a | 0.13 | 150 | None | 453 | 8.0 | 16 |
| Example 5-5 | 9.9% by weight $WO_X$—Pd/C | Example 2a | 0.25 | 150 | None | 453 | 8.0 | 16 |
| Example 5-6 | 9.9% by weight $WO_X$—Pd/C | Example 30a | 0.5 | 150 | None | 453 | 8.0 | 16 |
| Example 5-7 | 9.9% by weight $WO_X$—Pd/C | Example 31a | 1 | 150 | None | 453 | 8.0 | 16 |
| Example 5-8 | 9.9% by weight $WO_X$—Pd/C | Example 32a | 2 | 150 | None | 453 | 8.0 | 16 |
| Example 5-9 | 1.4% by weight Pd/C | Example 33a | (0.25) | 150 | None | 453 | 8.0 | 16 |

TABLE 10

| | Conversion (%) | Selectivity (%) | | | | | | | | | | |
|---|---|---|---|---|---|---|---|---|---|---|---|---|
| | | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 5-1 | 16.5 | 16.0 | 47.8 | 5.7 | 0.0 | 0.0 | 2.9 | 0.0 | 6.0 | 0.0 | 2.5 | 19.1 |
| Example 5-2 | 51.6 | 1.3 | 63.8 | 2.0 | 0.0 | 0.0 | 12.2 | 0.0 | 0.9 | 0.3 | 0.9 | 18.6 |
| Example 5-3 | 50.0 | 2.5 | 65.3 | 0.5 | 0.0 | 0.0 | 5.9 | 0.0 | 0.5 | 0.0 | 0.5 | 24.9 |
| Example 5-4 | 50.5 | 5.7 | 64.8 | 0.6 | 0.0 | 0.0 | 6.7 | 0.0 | 0.4 | 0.0 | 0.8 | 20.9 |
| Example 5-5 | 43.7 | 8.3 | 68.9 | 1.2 | 0.0 | 0.0 | 9.5 | 0.0 | 0.7 | 0.0 | 1.1 | 10.2 |
| Example 5-6 | 36.8 | 7.8 | 70.0 | 1.9 | 0.0 | 0.0 | 5.0 | 0.0 | 0.5 | 0.0 | 2.4 | 12.4 |
| Example 5-7 | 30.8 | 7.7 | 73.6 | 0.9 | 0.0 | 0.0 | 3.6 | 0.0 | 0.4 | 0.0 | 2.9 | 10.8 |
| Example 5-8 | 19.7 | 6.8 | 75.2 | 0.0 | 0.0 | 0.0 | 0.0 | 0.0 | 0.0 | 0.0 | 8.7 | 9.3 |
| Example 5-9 | 1.0 | 10.7 | 12.6 | 0.0 | 0.0 | 0.0 | 0.0 | 0.0 | 0.0 | 0.0 | 24.4 | 52.3 |

Example 34a

Production of Catalyst (9.9% by Weight $WO_x$—Pd/C)

Ammonium tungstate (manufactured by Wako Pure Chemical Industries, Ltd.) (0.1402 g) was dissolved in 15 mL of distilled water at 70 to 90° C., to prepare an aqueous solution. In addition, an aqueous solution in which 0.2818 g of an aqueous palladium (II) nitrate solution (Pd: 5.07%, manufactured by N. E. Chemcat Corporation) was diluted with 5 mL of distilled water was prepared. Then, the total amount of the aqueous ammonium tungstate solution was added to 0.8870 g of carbon black (product name "Vulcan XC72", manufactured by Cabot Corporation) in five portions so that no liquid pool was made, and the resultant was heated and stirred at 70 to 90° C. for impregnation. After this resultant was dried in a dryer at 110° C. overnight, the total amount of the dilute aqueous palladium (II) nitrate solution was added thereto in two portions so that no liquid pool was made, and the resultant was heated and stirred at 70 to 90° C. for impregnation. After such impregnation, the resultant was dried in a dryer at 110° C. overnight.

Then, the total amount of the resultant was packed in a flow-through type catalytic reduction apparatus having an inner diameter of 0.6 cm, and the temperature was raised at a rate of 10° C./min., while hydrogen was allowed to flow through at 30 cc/min. After the temperature reached 300° C., that temperature was maintained for 30 minutes to perform a reduction treatment.

Thereafter, the resultant was cooled to room temperature over 30 minutes, hydrogen was then switched to a 2% oxygen (balance: He) gas, and passivation was performed for 2 hours to provide a catalyst (9.9% by weight $WO_x$—Pd/C).

Example 35a

Production of Catalyst (9.9% by Weight $WO_x$—Pd/C)

Ammonium tungstate (manufactured by Wako Pure Chemical Industries, Ltd.) (0.1402 g) was dissolved in 15 mL of distilled water at 70 to 90° C., to prepare an aqueous solution. In addition, an aqueous solution in which 0.2818 g of an aqueous palladium (II) nitrate solution (Pd: 5.07%, manufactured by N. E. Chemcat Corporation) was diluted with 5 mL of distilled water was prepared. Then, the total amount of the aqueous ammonium tungstate solution was added to 0.8870 g of carbon black (product name "Vulcan XC72", manufactured by Cabot Corporation) in five portions so that no liquid pool was made, and the resultant was heated and stirred at 70 to 90° C. for impregnation. After this resultant was dried in a dryer at 110° C. overnight, the total amount of the dilute aqueous palladium (II) nitrate solution was added thereto in two portions so that no liquid pool was made, and the resultant was heated and stirred at 70 to 90° C. for impregnation. After such impregnation, the resultant was dried in a dryer at 110° C. overnight.

Then, the total amount of the resultant was packed in a flow-through type catalytic reduction apparatus having an inner diameter of 0.6 cm, and the temperature was raised at a rate of 10° C./min., while hydrogen was allowed to flow through at 30 cc/min. After the temperature reached 500° C., that temperature was maintained for 30 minutes to perform a reduction treatment.

Thereafter, the resultant was cooled to room temperature over 30 minutes, hydrogen was then switched to a 2% oxygen (balance: He) gas, and passivation was performed for 2 hours to provide a catalyst (9.9% by weight $WO_x$—Pd/C).

Examples 6-1 to 6-3

Production of 3-hydroxytetrahydrofuran was performed in the same manner as in Example 1-1 except that the catalyst used was changed to each catalyst shown in Table 11. The results are shown in Table 12.

TABLE 11

| | Catalyst | | Pd/W Molar ratio | Amount of catalyst (mg) | Reduction treatment (K) | Reaction temperature (K) | Hydrogen pressure (MPa) | Reaction time (h) |
|---|---|---|---|---|---|---|---|---|
| | Structure | Production | | | | | | |
| Example 6-1 | 9.9% by weight $WO_X$—Pd/C | Example 2a | 0.25 | 150 | None | 453 | 8.0 | 16 |
| Example 6-2 | 9.9% by weight $WO_X$—Pd/C | Example 34a | 0.25 | 150 | 573 | 453 | 8.0 | 16 |
| Example 6-3 | 9.9% by weight $WO_X$—Pd/C | Example 35a | 0.25 | 150 | 773 | 453 | 8.0 | 16 |

TABLE 12

| | Conversion (%) | Selectivity (%) | | | | | | | | | | |
|---|---|---|---|---|---|---|---|---|---|---|---|---|
| | | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 6-1 | 43.7 | 8.3 | 68.9 | 1.2 | 0.0 | 0.0 | 9.5 | 0.0 | 0.7 | 0.0 | 1.1 | 10.2 |
| Example 6-2 | 44.3 | 7.7 | 69.1 | 0.7 | 0.0 | 0.0 | 6.6 | 0.0 | 0.5 | 0.0 | 1.4 | 14.0 |
| Example 6-3 | 53.6 | 2.4 | 65.8 | 1.5 | 0.0 | 0.0 | 10.5 | 0.0 | 1.3 | 0.4 | 1.3 | 16.7 |

Examples 7-1 to 7-4

Production of 3-hydroxytetrahydrofuran was performed in the same manner as in Example 1-1 except that the catalyst used was changed to each catalyst shown in Table 13 and the amount of the catalyst used was changed as shown in Table 13. The results are shown in Table 14.

TABLE 13

| | Catalyst | | Pd/W Molar ratio | Amount of catalyst (mg) | Reduction treatment (K) | Reaction temperature (K) | Hydrogen pressure (MPa) | Reaction time (h) |
|---|---|---|---|---|---|---|---|---|
| | Structure | Production | | | | | | |
| Example 7-1 | 9.9% by weight $WO_X$—Pd/C | Example 2a | 0.25 | 50 | None | 453 | 8.0 | 16 |
| Example 7-2 | 9.9% by weight $WO_X$—Pd/C | Example 2a | 0.25 | 150 | None | 453 | 8.0 | 16 |
| Example 7-3 | 9.9% by weight $WO_X$—Pd/C | Example 2a | 0.25 | 300 | None | 453 | 8.0 | 16 |
| Example 7-4 | 9.9% by weight $WO_X$—Pd/C | Example 2a | 0.25 | 450 | None | 453 | 8.0 | 16 |

TABLE 14

| | Conversion (%) | Selectivity (%) | | | | | | | | | | |
|---|---|---|---|---|---|---|---|---|---|---|---|---|
| | | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 7-1 | 17.2 | 3.9 | 69.1 | 0.0 | 0.0 | 0.0 | 5.3 | 0.0 | 0.0 | 0.0 | 2.1 | 19.7 |
| Example 7-2 | 44.3 | 7.7 | 69.1 | 0.7 | 0.0 | 0.0 | 6.6 | 0.0 | 0.5 | 0.0 | 1.4 | 14.0 |
| Example 7-3 | 62.0 | 10.6 | 71.6 | 0.5 | 0.0 | 0.0 | 3.9 | 0.0 | 0.4 | 0.0 | 0.3 | 12.7 |
| Example 7-4 | 72.1 | 12.3 | 71.1 | 0.5 | 0.0 | 0.0 | 3.3 | 0.0 | 0.5 | 0.2 | 0.3 | 11.9 |

Examples 8-1 to 8-4

Production of 3-hydroxytetrahydrofuran was performed in the same manner as in Example 1-1 except that the catalyst used was changed to each catalyst shown in Table 15 and zeolite (H-ZSM-5) coexisted in the reaction system in each amount shown in Table 15. The results are shown in Table 16.

TABLE 15

| | Catalyst | | Pd/W Molar ratio | Amount of catalyst (mg) | Reduction treatment (K) | H-ZSM-5 (mg) | Reaction temperature (K) | Hydrogen pressure (MPa) | Reaction time (h) |
|---|---|---|---|---|---|---|---|---|---|
| | Structure | Production | | | | | | | |
| Example 8-1 | 9.9% by weight $WO_X$—Pd/C | Example 2a | 0.25 | 150 | None | 0 | 453 | 8.0 | 16 |
| Example 8-2 | 9.9% by weight $WO_X$—Pd/C | Example 2a | 0.25 | 150 | None | 10 | 453 | 8.0 | 16 |
| Example 8-3 | 9.9% by weight $WO_X$—Pd/C | Example 2a | 0.25 | 150 | None | 50 | 453 | 8.0 | 16 |
| Example 8-4 | 9.9% by weight $WO_X$—Pd/C | Example 2a | 0.25 | 150 | None | 150 | 453 | 8.0 | 16 |

TABLE 16

| | Conversion (%) | Selectivity (%) | | | | | | | | | | |
|---|---|---|---|---|---|---|---|---|---|---|---|---|
| | | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 8-1 | 44.3 | 7.7 | 69.1 | 0.7 | 0.0 | 0.0 | 6.6 | 0.0 | 0.5 | 0.0 | 1.4 | 14.0 |
| Example 8-2 | 47.8 | 6.0 | 66.8 | 1.5 | 0.0 | 0.0 | 10.3 | 0.0 | 1.0 | 0.4 | 1.7 | 12.3 |
| Example 8-3 | 48.7 | 5.9 | 72.1 | 0.4 | 0.0 | 0.0 | 5.4 | 0.0 | 0.3 | 0.0 | 0.9 | 15.0 |
| Example 8-4 | 49.6 | 8.6 | 74.3 | 0.0 | 0.0 | 0.0 | 2.3 | 0.0 | 0.3 | 0.0 | 1.4 | 13.1 |

Examples 9-1 to 9-6

Production of 3-hydroxytetrahydrofuran was performed in the same manner as in Example 1-1 except that the catalyst used was changed to each catalyst shown in Table 17 and the reaction temperature and the reaction time were changed as shown in Table 17. The results are shown in Table 18.

TABLE 17

| | Catalyst | | Pd/W Molar ratio | Amount of catalyst (mg) | Reduction treatment (K) | Reaction temperature (K) | Hydrogen pressure (MPa) | Reaction time (h) |
|---|---|---|---|---|---|---|---|---|
| | Structure | Production | | | | | | |
| Example 9-1 | 9.9% by weight $WO_X$—Pd/C | Example 2a | 0.25 | 150 | None | 413 | 8.0 | 16 |
| Example 9-2 | 9.9% by weight $WO_X$—Pd/C | Example 2a | 0.25 | 150 | None | 433 | 8.0 | 16 |
| Example 9-3 | 9.9% by weight $WO_X$—Pd/C | Example 2a | 0.25 | 150 | None | 453 | 8.0 | 16 |
| Example 9-4 | 9.9% by weight $WO_X$—Pd/C | Example 2a | 0.25 | 150 | None | 473 | 8.0 | 16 |
| Example 9-5 | 9.9% by weight $WO_X$—Pd/C | Example 2a | 0.25 | 150 | None | 493 | 8.0 | 4 |
| Example 9-6 | 9.9% by weight $WO_X$—Pd/C | Example 2a | 0.25 | 150 | None | 513 | 8.0 | 4 |

TABLE 18

| | Conversion (%) | Selectivity (%) | | | | | | | | | | |
|---|---|---|---|---|---|---|---|---|---|---|---|---|
| | | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 9-1 | 2.1 | 6.5 | 51.7 | 0.0 | 0.0 | 0.0 | 0.0 | 0.0 | 0.0 | 0.0 | 0.0 | 41.8 |
| Example 9-2 | 11.3 | 11.6 | 68.4 | 0.0 | 0.0 | 0.0 | 2.9 | 0.0 | 1.7 | 0.0 | 1.8 | 13.7 |
| Example 9-3 | 43.7 | 8.3 | 68.9 | 1.2 | 0.0 | 0.0 | 9.5 | 0.0 | 0.7 | 0.0 | 1.1 | 10.2 |
| Example 9-4 | 93.6 | 10.6 | 69.5 | 0.6 | 0.0 | 0.0 | 7.3 | 0.0 | 1.2 | 0.7 | 0.6 | 9.5 |
| Example 9-5 | 99.7 | 10.5 | 70.4 | 0.0 | 0.0 | 0.0 | 1.3 | 0.0 | 0.7 | 0.2 | 0.5 | 16.3 |
| Example 9-6 | 100.0 | 24.3 | 61.1 | 0.0 | 0.0 | 0.0 | 0.5 | 0.0 | 2.9 | 0.9 | 0.3 | 10.0 |

Examples 10-1 to 10-6

Production of 3-hydroxytetrahydrofuran was performed in the same manner as in Example 1-1 except that the catalyst used was changed to each catalyst shown in Table 19, the reaction time was changed as shown in Table 19, and the amount of 1,4-dioxane used (namely, concentration of 1,4-anhydroerythritol) was changed as shown in Table 19. The results are shown in Table 20.

TABLE 19

| | Catalyst | | Pd/W Molar ratio | Amount of catalyst (mg) | Reduction treatment (K) | Reaction temperature (K) | Hydrogen pressure (MPa) | Reaction time (h) | 1,4-AHTRE Concentration (%) | 1,4-Dioxane (g) |
|---|---|---|---|---|---|---|---|---|---|---|
| | Structure | Production | | | | | | | | |
| Example 10-1 | 9.9% by weight $WO_X$—Pd/C | Example 2a | 0.25 | 150 | None | 453 | 8.0 | 4 | 5 | 19 |
| Example 10-2 | 9.9% by weight $WO_X$—Pd/C | Example 2a | 0.25 | 150 | None | 453 | 8.0 | 4 | 10 | 9 |
| Example 10-3 | 9.9% by weight $WO_X$—Pd/C | Example 2a | 0.25 | 150 | None | 453 | 8.0 | 4 | 20 | 4 |
| Example 10-4 | 9.9% by weight $WO_X$—Pd/C | Example 2a | 0.25 | 150 | None | 453 | 8.0 | 4 | 50 | 1 |
| Example 10-5 | 9.9% by weight $WO_X$—Pd/C | Example 2a | 0.25 | 150 | None | 453 | 8.0 | 4 | 80 | 0.25 |
| Example 10-6 | 9.9% by weight $WO_X$—Pd/C | Example 2a | 0.25 | 150 | None | 453 | 8.0 | 4 | 100 | 0 |

TABLE 20

| | Conversion (%) | Selectivity (%) | | | | | | | | | | |
|---|---|---|---|---|---|---|---|---|---|---|---|---|
| | | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 10-1 | 4.7 | 8.7 | 33.0 | 0.0 | 0.0 | 0.0 | 0.0 | 0.0 | 0.0 | 0.0 | 0.0 | 58.3 |
| Example 10-2 | 10.1 | 5.8 | 62.2 | 0.0 | 0.0 | 0.0 | 0.0 | 0.0 | 0.0 | 0.0 | 1.4 | 30.5 |
| Example 10-3 | 16.9 | 6.4 | 69.4 | 0.0 | 0.0 | 0.0 | 1.5 | 0.0 | 0.0 | 0.0 | 1.1 | 21.6 |
| Example 10-4 | 22.6 | 6.8 | 75.4 | 0.0 | 0.0 | 0.0 | 6.6 | 0.0 | 0.0 | 0.0 | 0.9 | 10.3 |
| Example 10-5 | 25.1 | 6.1 | 76.7 | 0.0 | 0.0 | 0.0 | 5.2 | 0.0 | 0.0 | 0.0 | 0.9 | 11.2 |
| Example 10-6 | 27.2 | 2.0 | 54.7 | 0.0 | 0.0 | 0.0 | 0.0 | 0.0 | 0.0 | 0.0 | 0.0 | 43.2 |

Examples 11-1 to 11-3

Production of 3-hydroxytetrahydrofuran was performed in the same manner as in Example 1-1 except that the catalyst used was changed to each catalyst shown in Table 21, the amount of 1,4-dioxane used was changed to 1 g, and the reaction time and the hydrogen pressure were changed as shown in Table 21. The results are shown in Table 22.

TABLE 21

| | Catalyst | | Pd/W Molar ratio | Amount of catalyst (mg) | Reduction treatment (K) | Reaction temperature (K) | Hydrogen pressure (MPa) | Reaction time (h) |
|---|---|---|---|---|---|---|---|---|
| | Structure | Production | | | | | | |
| Example 11-1 | 9.9% by weight $WO_x$—Pd/C | Example 2a | 0.25 | 150 | None | 453 | 4 | 4 |
| Example 11-2 | 9.9% by weight $WO_x$—Pd/C | Example 2a | 0.25 | 150 | None | 453 | 8 | 4 |
| Example 11-3 | 9.9% by weight $WO_x$—Pd/C | Example 2a | 0.25 | 150 | None | 453 | 12 | 4 |

TABLE 22

| | Conversion (%) | Selectivity (%) | | | | | | | | | | |
|---|---|---|---|---|---|---|---|---|---|---|---|---|
| | | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 11-1 | 25.2 | 3.6 | 59.9 | 0.0 | 0.0 | 0.0 | 0.0 | 0.0 | 0.0 | 0.0 | 0.0 | 36.5 |
| Example 11-2 | 22.6 | 6.8 | 75.4 | 0.0 | 0.0 | 0.0 | 6.6 | 0.0 | 0.0 | 0.0 | 0.9 | 10.3 |
| Example 11-3 | 24.1 | 4.8 | 74.8 | 0.0 | 0.0 | 0.0 | 5.0 | 0.0 | 0.0 | 0.0 | 0.9 | 14.5 |

Examples 12-1 to 12-4

Production of 3-hydroxytetrahydrofuran was performed in the same manner as in Example 1-1 except that the catalyst used was changed to each catalyst shown in Table 23 and the reaction time was changed as shown in Table 23. The results are shown in Table 24.

TABLE 23

| | Catalyst | | Pd/W Molar ratio | Amount of catalyst (mg) | Reduction treatment (K) | Reaction temperature (K) | Hydrogen pressure (MPa) | Reaction time (h) |
|---|---|---|---|---|---|---|---|---|
| | Structure | Production | | | | | | |
| Example 12-1 | 9.9% by weight $WO_x$—Pd/C | Example 2a | 0.25 | 150 | None | 453 | 8.0 | 4 |
| Example 12-2 | 9.9% by weight $WO_x$—Pd/C | Example 2a | 0.25 | 150 | None | 453 | 8.0 | 16 |
| Example 12-3 | 9.9% by weight $WO_x$—Pd/C | Example 2a | 0.25 | 150 | None | 453 | 8.0 | 32 |
| Example 12-4 | 9.9% by weight $WO_x$—Pd/C | Example 2a | 0.25 | 150 | None | 453 | 8.0 | 48 |

TABLE 24

|  | Conversion (%) | Selectivity (%) | | | | | | | | | | |
|---|---|---|---|---|---|---|---|---|---|---|---|---|
|  |  | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 12-1 | 16.9 | 6.4 | 69.4 | 0.0 | 0.0 | 0.0 | 1.5 | 0.0 | 0.0 | 0.0 | 1.1 | 21.6 |
| Example 12-2 | 44.3 | 7.7 | 69.1 | 0.7 | 0.0 | 0.0 | 6.6 | 0.0 | 0.5 | 0.0 | 1.4 | 14.0 |
| Example 12-3 | 64.8 | 6.6 | 70.2 | 0.6 | 0.0 | 0.0 | 7.5 | 0.0 | 0.6 | 0.3 | 0.8 | 13.3 |
| Example 12-4 | 71.8 | 6.2 | 67.9 | 0.9 | 0.0 | 0.0 | 10.9 | 0.0 | 1.0 | 0.5 | 0.8 | 11.9 |

Example 13-1

Production of 3-hydroxytetrahydrofuran was performed in the same manner as in Example 1-2. The results are shown in Table 26.

Comparative Examples 1 to 3

Production of 3-hydroxytetrahydrofuran was performed in the same manner as in Example 13-1 except that the catalyst used was changed to each catalyst shown in Table 25 and each reaction substrate shown in Table 25 was used instead of 1,4-anhydroerythritol. The results are shown in Table 26.

TABLE 25

|  | Catalyst | | Pd/W Molar ratio | Amount of catalyst (mg) | Reduction treatment (K) | Reaction temperature (K) | Hydrogen pressure (MPa) | Reaction time (h) | Substrate |
|---|---|---|---|---|---|---|---|---|---|
|  | Structure | Production |  |  |  |  |  |  |  |
| Example 13-1 | 9.9% by weight $WO_X$—Pd/C | Example 2a | 0.25 | 150 | None | 453 | 8.0 | 16 | 1,4-AHTRE |
| Comparative Example 1 | 9.9% by weight $WO_X$—Pd/C | Example 2a | 0.25 | 150 | None | 453 | 8.0 | 16 | 3-HTHF |
| Comparative Example 2 | 9.9% by weight $WO_X$—Pd/C | Example 2a | 0.25 | 150 | None | 453 | 8.0 | 16 | THE |
| Comparative Example 3 | 9.9% by weight $WO_X$—Pd/C | Example 2a | 0.25 | 150 | None | 453 | 8.0 | 16 | None |

TABLE 26

|  | Conversion (%) | Selectivity (%) | | | | | | | | | | |
|---|---|---|---|---|---|---|---|---|---|---|---|---|
|  |  | THF | 3-HTHF | 1,4-BuD | 1,2,3-BuT | 1,3-BuD | 1,2-BuD | 2,3-BuD | 1-BuOH | 2-BuOH | 1,4-AHTRE | Others |
| Example 13-1 | 44.3 | 7.7 | 69.1 | 0.7 | 0.0 | 0.0 | 6.6 | 0.0 | 0.5 | 0.0 | 1.4 | 14.0 |
| Comparative Example 1 | 0.6 | 55.7 | 0.0 | 0.0 | 0.0 | 0.0 | 0.0 | 0.0 | 0.0 | 0.0 | 0.0 | 44.3 |
| Comparative Example 2 | 1.9 | 0.0 | 0.0 | 0.0 | 0.0 | 0.0 | 0.0 | 0.0 | 93.9 | 0.0 | 0.0 | 6.1 |
| Comparative Example 3 | 0.0 | 0.0 | 0.0 | 0.0 | 0.0 | 0.0 | 0.0 | 0.0 | 0.0 | 0.0 | 0.0 | 0.0 |

Example 36a

Preparation of Catalyst (4% by Weight Ir—$ReO_X$/$SiO_2$)

Silicon dioxide ($SiO_2$) (product name "G-6", manufactured by Fuji Silysia Chemical Ltd., specific surface area: 535 m²/g) was used as the carrier of the catalyst. An aqueous chloroiridic acid ($H_2IrCl_6$) solution prepared so as to have an iridium (Ir) concentration of 4.47% by weight was dropped to the carrier, the whole of the carrier was swollen, and thereafter the carrier was dried at 110° C. for 3 hours. Then, such dropping of the aqueous chloroiridic acid solution and such drying of the resulting carrier were repeated to allow iridium to be supported so that the amount of iridium was 4% by weight relative to $SiO_2$.

Then, an aqueous ammonium perrhenate ($NH_4ReO_4$) solution prepared so as to have a rhenium (Re) concentration of 3% by weight was dropped to the carrier (carrier with iridium supported thereon) and the carrier was dried repeatedly as in the dropping of the aqueous chloroiridic acid solution and the drying of the resulting carrier, to allow rhenium to be supported so that the molar ratio of rhenium to iridium [Re/Ir] was 2/1. Thereafter, the carrier dried was fired in an air atmosphere (in the air) under conditions of 500° C. and 3 hours, to prepare a catalyst (4% by weight Ir—$ReO_X$/$SiO_2$).

Example 14-1

Production of 1,3-butane diol

An inner glass cylinder for an autoclave was charged with a stirrer chip, 150 mg of the catalyst (4% by weight Ir—ReO$_x$/SiO$_2$) obtained in Example 36a, and 4 g of water. The inner cylinder for an autoclave was placed in an autoclave, and the lid of the autoclave was closed. Then, an operation of feeding 1 MPa of hydrogen into the autoclave and thereafter evacuating the atmosphere in the autoclave was repeated three times, to expel the air in the autoclave from the autoclave. The autoclave was filled with hydrogen so that a pressure of 8 MPa was shown at the reduction temperature of 200° C. and a pressure of 5 MPa was shown at room temperature.

Subsequently, the autoclave was set to a heating apparatus equipped with a magnetic stirrer, and maintained for 1 hour while heating so that the temperature in the reactor (in the autoclave) was 200° C., to reduce the catalyst.

Subsequently, the autoclave was cooled to room temperature once, hydrogen was released, and 1 g of 3-hydroxytetrahydrofuran was introduced. Then, the operation of feeding 1 MPa of hydrogen into the autoclave and thereafter evacuating the atmosphere in the autoclave was again repeated three times, to expel the air in the autoclave from the autoclave. Thereafter, the autoclave was filled with hydrogen so that a pressure of 1 MPa was shown at room temperature, and thereafter was heated to 100° C. After the temperature reached 100° C., hydrogen was introduced so that a pressure of 8 MPa was shown, and maintained for 6 hours.

Thereafter, the temperature was decreased to room temperature, and hydrogen in the autoclave was released for pressure release.

(Analysis of Products)

With respect to the solution after the reaction, products were quantitatively analyzed using gas chromatography (gas chromatographic apparatus: "GC-2014" (manufactured by Shimadzu Corporation), GC column: TC-WAX, DB-FFAP, detector: FID), and the conversion of 3-hydroxytetrahydrofuran, and the selectivity of each of tetrahydrofuran, 1,4-butane diol, 1,2,3-butane triol, 1,2-butane diol, 2,3-butane diol, 1-butanol, 2-butanol, 1,4-anhydroerythritol and other products were calculated. The results are shown in Table 27. Herein, these products were identified by GC-MS ("QP5050", manufactured by Shimadzu Corporation).

Examples 14-2 to 14-4

Production of 1,3-propane diol and analysis of each of products were performed in the same manner as in Example 14-1 except that the reaction time was changed as shown in Table 27. The results are shown in Table 27.

TABLE 27

| | Catalyst | Re/Ir Molar ratio | Reaction time (h) | Conversion % | Selectivity (%) THF | 1,4-BuD |
|---|---|---|---|---|---|---|
| Example 14-1 | 4% by weight Ir—ReO$_x$/SiO$_2$ | 2 | 6 | 23.9 | 2.1 | 0.0 |
| Example 14-2 | 4% by weight Ir—ReO$_x$/SiO$_2$ | 2 | 12 | 49.7 | 2.8 | 0.0 |
| Example 14-3 | 4% by weight Ir—ReO$_x$/SiO$_2$ | 2 | 24 | 70.1 | 2.3 | 0.0 |
| Example 14-4 | 4% by weight Ir—ReO$_x$/SiO$_2$ | 2 | 36 | 87.7 | 3.4 | 0.0 |

| | Selectivity (%) | | | | | | | |
|---|---|---|---|---|---|---|---|---|
| | 1,2,3-BuT | 1,3-BuD | 1,2-BuD | 2,3-BuD | 1-BuOH | 2-BuOH | 1,4-AHTRE | Others |
| Example 14-1 | 0.0 | 81.1 | 0.0 | 0.0 | 7.0 | 9.5 | 0.0 | 0.3 |
| Example 14-2 | 0.0 | 72.0 | 0.0 | 0.0 | 11.5 | 13.4 | 0.0 | 0.3 |
| Example 14-3 | 0.0 | 58.6 | 0.0 | 0.0 | 17.9 | 20.4 | 0.0 | 0.8 |
| Example 14-4 | 0.0 | 42.8 | 0.0 | 0.0 | 23.2 | 28.2 | 0.0 | 2.4 |

Production Example 1

Production of 1,4-Anhydroerythritol: Dehydration Reaction Step

One gram of erythritol, 4 g of water and 0.15 g of "Amberlyst 70" (product name) as a catalyst were placed in an autoclave, and reacted under conditions of an argon pressure of 5 MPa, 160° C., and 24 hours, to provide 1,4-anhydroerythritol. The conversion of erythritol was 98.6%, and the selectivity of 1,4-anhydroerythritol was 97.2%.

Abbreviations in Tables represent the following respective compounds.
THF: tetrahydrofuran
3-HTHF: 3-hydroxytetrahydrofuran
1,4-BuD: 1,4-butane diol
1,2,3-BuT: 1,2,3-butane triol
1,3-BuD: 1,3-butane diol
1,2-BuD: 1,2-butane diol
2,3-BuD: 2,3-butane diol
1-BuOH: 1-butanol
2-BuOH: 2-butanol
1,4-AHTRE: 1,4-anhydroerythritol
Others: other compounds

REFERENCE SIGNS LIST

1: trickle bed reactor
2: raw material liquid supply line
3: hydrogen supply line
4: reaction mixture-ejecting line
5: high-pressure gas-liquid separator
6: hydrogen recycle line

INDUSTRIAL APPLICABILITY

The method for producing 3-hydroxytetrahydrofuran of the present invention is a method for producing 3-hydroxytetrahydrofuran using, as a raw material, 1,4-anhydroerythritol that can be easily derived from erythritol of biomass. In addition, the method for producing 1,3-butane diol of the present invention is a method for producing 1,3-butane diol using such 3-hydroxytetrahydrofuran as a raw material. 1,3-Butane diol obtained by such a method can be incorporated as a moisturizer into cosmetics, detergents, shampoos, and the like, and is also expected to be used as a raw material for medicines, food additives, various solvents, and the like.

The invention claimed is:

1. A method for producing 3-hydroxytetrahydrofuran, comprising a step of reacting 1,4-anhydroerythritol and hydrogen to produce 3-hydroxytetrahydrofuran,
    wherein the step of reacting 1,4-anhydroerythritol and hydrogen is allowed to proceed in the presence of a catalyst comprising a carrier and at least one oxide selected from the group consisting of an oxide of a Group 6 element and an oxide of a Group 7 element, the oxide being supported on the carrier wherein the oxide of a Group 6 element is selected from the group consisting of chromium, molybdenum, tungsten and seaborgium oxide, and wherein the oxide of a Group 7 element is selected from the group consisting of manganese, technetium and bohrium oxide.

2. The method for producing 3-hydroxytetrahydrofuran according to claim 1, wherein the carrier is activated carbon or an inorganic oxide.

3. The method for producing 3-hydroxytetrahydrofuran according to claim 1, wherein the catalyst further comprises a metal other than a Group 6 element and a Group 7 element, the other metal being supported on the carrier.

4. The method for producing 3-hydroxytetrahydrofuran according to claim 3, wherein the other metal is at least one metal selected from the group consisting of palladium, platinum, iron, cobalt, nickel and copper.

5. The method for producing 3-hydroxytetrahydrofuran according to claim 2, wherein the inorganic oxide is at least one inorganic oxide selected from the group consisting of titania, zirconia, magnesia, silica and alumina.

6. The method for producing 3-hydroxytetrahydrofuran according to claim 1, wherein the carrier is activated carbon.

7. The method for producing 3-hydroxytetrahydrofuran according to claim 3, wherein the other metal is palladium.

8. The method for producing 3-hydroxytetrahydrofuran according to claim 1, wherein the oxide is an oxide of a Group 6 element.

9. The method for producing 3-hydroxytetrahydrofuran according to claim 1, wherein the oxide is tungsten oxide.

10. The method for producing 3-hydroxytetrahydrofuran according to claim 1, wherein the amount of the oxide supported on the carrier in terms of the Group 6 element and Group 7 element forming the oxide is 0.01 to 50% by weight based on the total amount of the oxide and the carrier being 100% by weight.

11. The method for producing 3-hydroxytetrahydrofuran according to claim 3, wherein the amount of the oxide supported on the carrier in terms of the Group 6 element and Group 7 element forming the oxide is 0.01 to 50% by weight based on the total amount of the oxide and the carrier being 100% by weight.

12. The method for producing 3-hydroxytetrahydrofuran according to claim 3, wherein the molar ratio in terms of metal of the other metal to the Group 6 element and Group 7 element forming the oxide [other metal/Group 6 element and Group 7 element] is 50/1 to 1/500.

13. The method for producing 3-hydroxytetrahydrofuran according to claim 11, wherein the molar ratio in terms of metal of the other metal to the Group 6 element and Group 7 element forming the oxide [other metal/Group 6 element and Group 7 element] is 50/1 to 1/500.

14. The method for producing 3-hydroxytetrahydrofuran according to claim 3,
    wherein the oxide is tungsten oxide,
    the carrier is activated carbon, and
    the other metal is palladium.

15. The method for producing 3-hydroxytetrahydrofuran according to claim 12,
    wherein the oxide is tungsten oxide,
    the carrier is activated carbon, and
    the other metal is palladium.

16. The method for producing 3-hydroxytetrahydrofuran according to claim 13,
    wherein the oxide is tungsten oxide,
    the carrier is activated carbon, and
    the other metal is palladium.

* * * * *